(12) United States Patent
Abell

(10) Patent No.: US 8,417,342 B1
(45) Date of Patent: Apr. 9, 2013

(54) GASTROINTESTINAL ELECTRICAL STIMULATION DEVICE AND METHOD FOR TREATING GASTROINTESTINAL DISORDERS

(75) Inventor: Thomas Abell, Ridgeland, MS (US)

(73) Assignee: University of Mississippi Medical Center, Jackson, MS (US)

( * ) Notice: Subject to any disclaimer, the term of this patent is extended or adjusted under 35 U.S.C. 154(b) by 1098 days.

(21) Appl. No.: 12/256,789

(22) Filed: Oct. 23, 2008

Related U.S. Application Data

(63) Continuation-in-part of application No. 11/773,250, filed on Jul. 3, 2007.

(51) Int. Cl.
*A61N 1/00* (2006.01)

(52) U.S. Cl.
USPC .......................................................... 607/40

(58) Field of Classification Search .................. None
See application file for complete search history.

(56) References Cited

U.S. PATENT DOCUMENTS

| | | | |
|---|---|---|---|
| 4,682,601 A * | 7/1987 | Tagliavini | 607/72 |
| 5,292,344 A | 3/1994 | Douglas | |
| 5,690,691 A | 11/1997 | Chen et al. | |
| 6,132,372 A | 10/2000 | Essen-Moller | |
| 6,542,776 B1 | 4/2003 | Gordon et al. | |
| 6,689,056 B1 | 2/2004 | Kilcoyne et al. | |
| 6,826,428 B1 * | 11/2004 | Chen et al. | 607/40 |
| 6,895,279 B2 | 5/2005 | Loeb et al. | |
| 7,016,735 B2 | 3/2006 | Imran et al. | |
| 7,020,531 B1 | 3/2006 | Colliou et al. | |
| 7,249,145 B1 | 7/2007 | Rock et al. | |
| 7,483,746 B2 | 1/2009 | Lee et al. | |
| 7,580,751 B2 | 8/2009 | Starkebaum | |

(Continued)

FOREIGN PATENT DOCUMENTS

| | | | |
|---|---|---|---|
| AU | 200193039 A * | 4/2002 | |
| CN | 1476339 A * | 2/2004 | |

(Continued)

OTHER PUBLICATIONS

Misiara, Gustavo et al., "Dynamic antral scintigraphy following solid and liquid meals in healthy human subjects", Nuclear medicine communications (England), Jun. 2007, 28 (6) p. 479-83.*

(Continued)

*Primary Examiner* — Eric D Bertram
*Assistant Examiner* — Elizabeth K So
(74) *Attorney, Agent, or Firm* — Stites & Harbison PLLC; Stephen Weyer

(57) ABSTRACT

A device and method is provided for treating treat gastrointestinal disorders using electrical stimulation. In one advantageous form, the method uses mucosal EGG (mEGG) to analyze a patient's natural gastric electrical activity. The mEGG can be measured anywhere in the gastrointestinal tract. From the mEGG, one can determine whether a patient is a good candidate for gastrointestinal electrical stimulation. For example, analysis of the frequency, amplitude and a ratio of frequency to amplitude can be used to determine who should receive gastrointestinal electrical stimulation, and at what the various stimulation parameters should be. The present method can be used to treat various disorders relating to gastrointestinal electrical activity. Ideally, the gastric electrical stimulation is delivered at a desired frequency and amplitude to effectuate normalization of gastric electrical current/activity, thereby treating disorders associated with gastric electrical activity. Advantageously, gastrointestinal electrical stimulation is effectuated by endoscopically delivering the electrostimulating device.

8 Claims, 12 Drawing Sheets

U.S. PATENT DOCUMENTS

| | | | |
|---|---|---|---|
| 7,941,221 B2* | 5/2011 | Foley | 607/40 |
| 2002/0103522 A1 | 8/2002 | Swoyer et al. | |
| 2004/0093039 A1 | 5/2004 | Schumert | |
| 2004/0162595 A1* | 8/2004 | Foley | 607/40 |
| 2006/0161217 A1 | 7/2006 | Jaax et al. | |
| 2007/0255337 A1* | 11/2007 | Lu | 607/40 |
| 2007/0276204 A1* | 11/2007 | Eide | 600/301 |
| 2010/0152644 A1* | 6/2010 | Pesach et al. | 604/20 |

FOREIGN PATENT DOCUMENTS

| | | | |
|---|---|---|---|
| EP | 1322380 A | * | 7/2003 |
| JP | 8224215 A | * | 9/1996 |
| JP | 2004509714 W | * | 4/2004 |
| JP | 3729209 B2 | * | 12/2005 |
| RU | 2267986 C1 | * | 1/2006 |
| WO | WO 0226317 A1 | * | 4/2002 |

OTHER PUBLICATIONS

Kara, Sadik et al., "Detection of gastric dysrhythmia using WT and ANN in diabetic gastroparesis patients", Computers in biology and medicine (United States), Mar. 2003, 36 (3) p. 276-90.*

Urbain, J L et al., "Recent advances in gastric emptying scintigraphy", Seminars in nuclear medicine (United States), Oct. 1995, 25(4) p. 318-25.*

Garrick, T. et al., "Corticotropin-releasing factor acts on the brain to reduce gastric contractility", Psychotherapy and psychosomatics (Switzerland), 1987, 48 (1-4) p. 14-20.*

Abid, Shahab et al., "Poor correlation between electrogastrography and antroduodenal manometry in patients with motility disorders", Gastroenterology 130 (4, Suppl. 2): p. A433 Apr. 2006.*

Bradshaw, Leonard A. et al., "Glucagon alters frequency and propagation velocity of the gastric slow wave magnetic field", Gastroenterology 130 (4, Suppl. 2): p. A245 Apr. 2006.*

Abell, et al., Glucagon-Evoked Gastric Dysrhythmias in Humans Shown by an Improved Electrogastrographic Technique; Gastroenterology, vol. 88, 1985, pp. 932-940.

Abell, et al., Gastric electromechanical and neurohormonal function in anorexia nervosa; Gastroenterology, vol. 93, No. 5, Nov. 1987, pp. 958-965.

Abell, et al., Electrogastrography. Current assessment and future perspectives.; Dig. Dis. Sci., vol. 33, No. 8, Aug. 1988, pp. 982-992.

Abell, et al., Gastric electromechanical function and gastric emptying in diabetic gastroparesis; European Journal of Gastroenterology & Hepatology, vol. 3, 1991, pp. 163-167.

Abell, et al., Diabetic gastroparesis is associated with an abnormality in sympathetic innervation; European Journal of Gastroenterology & Hepatology, vol. 6, 1994, pp. 241-247.

Abell, et al., Gastric electrical stimulation in intractable symptomatic gastroparesis; Digestion, vol. 66, No. 4, 2002, pp. 204-212.

Abell, et al., Gastroparesis and the gastric pacemaker; a revolutionary treatment for an old disease [abstract]; J. Miss. State Med. Assoc., vol. 43, No. 12, Dec. 2002, pp. 369-375.

Abell, et al., Gastric electrical stimulation for gastroparesis improves nutritional parameters at short, intermediate, and long-term follow-up [abstract]; J. Parenter. Enteral. Nutr., vol. 27, No. 4, Jul.-Aug. 2003, pp. 277-281.

Abell, et al., Gastric electrical stimulation for medically refractory gastroparesis; Gastroenterology, vol. 126, No. 2, Aug. 2003, pp. 421-428.

Abell, et al., Nutrition Aspects of Gastroparesis and Therapies for Drug-Refractory Patients; Nutrition in Clinical Practice, vol. 21, Feb. 2006, pp. 23-33.

Abell, et al., Looking to the Future; Electrical Stimulation for Obesity [Bariatric Surgery]; The American Journal of the Medical Sciences, vol. 331, No. 6, Apr. 2006, pp. 226-232.

Abidi, et al., An energy algorithm improves symptoms in some patients with gastroparesis and treated with gastric electrical stimulation; Neurogastroenterol. Motil., vol. 18, No. 4, Apr. 2006, pp. 334-338.

Ayinala et al., Temporary gastric electrical stimulation with orally or peg-placed electrodes in patients with drug refractory gastroparesis; Gastrointestinal Endoscopy, vol. 61, Mar. 2005, pp. 455-461.

Batista, et al., Effects of Temporary Gastric Electrical Stimulation With Endoscopically Placed Electrodes: A Report of 41 Consecutive Patients [abstract]; American Society for Gastrointestinal Endoscopy, Apr. 2004.

Cutts, et al., Symptom improvement from prokinetic therapy corresponds to improved quality of life in patients with severe dyspepsia; Dig. Dis. Sci, vol. 41, No. 7, Jul. 1996, pp. 1369-1378.

Cutts, et al., Is gastric electrical stimulation superior to standard pharmacologic therapy in improving GI symptoms, healthcare resources, and long-term health care benefits?; Neurogastroenterol. Motil., vol. 17, No. 1, Feb. 2005, pp. 35-43.

Familoni, et al., Electrical stimulation at a frequency higher than basal rate in human stomach; Dig. Dis. Sci., vol. 42, No. 5, May 1997, pp. 885-891.

Familoni, et al., Efficacy of electrical stimulation at frequencies higher than basal rate in canine stomach; Dig. Dis. Sci., vol. 42, No. 5, May 1997, pp. 892-897.

Familoni, et al., Driving gastric electrical activity with electrical stimulation; Ann. Biomed. Eng., vol. 33, No. 3, Mar. 2005, pp. 356-364.

Gaber, et al., Improvement in Autonomic Function Following Combined Pancreas-Kidney Transplantation, vol. 23, No. 1, Feb. 1991, pp. 1660-1662.

Gaber, et al., Improved Autonomic and Gastric Function in Pancreas-Kidney vs Kidney-Alone Transplantation Contributes to Quality of Life; Transplantation Proceedings, vol. 26, No. 2, Apr. 1994, pp. 515-516.

Hathaway, et al., Improvement in Autonomic Function Following Pancreas-Kidney Versus Kidney-Alone Transplantation; Transplantation Proceedings, vol. 25, No. 1, Feb. 1993, pp. 1306-1308.

Hathaway, et al., Improvement in Autonomic and Gastric Function Following Pancreas-Kidney Versus Kidney-Alone Transplantation and the Correlations with Quality of Life; Transplantation, vol. 57, No. 6, Mar. 1994, pp. 816-822.

Luo, et al., Gastric electrical stimulation improves both GI symptoms and gastric emptying in patients with post-surgical gastroparesis [abstract]. Gastroenterology 1999; 116:S0162.

Luo, et al., Gastric Electrical Stimulation Is Associated With Improvement in Pancreatic Exocrine Function in Humans; Pancreas, vol. 29, No. 2, Aug. 2004, pp. e41-e44.

Rashed, et al., Autonomic Function in Cyclic Vomitin Syndrome and Classic Migraine; Digestive Diseases and Sciences, vol. 44, No. 8, Aug. 1999 Supplement, pp. 74S-78S.

Schmieg, et al., In Patients with Disordered Post-Surgical Gastric Emptying, Temporary Gastric Electrical Stimulation (TEMPGES) Quickly Improves Symptoms and Gastric Emptying; 45th Annual Meeting of the Society for Surgery of the Alimentary Tract, Publishing No. 543, May 18, 2004.

Office Action for U.S. Appl. No. 11/773,250 dated Jul. 6, 2009.

Office Action for U.S. Appl. No. 11/773,250 dated Jun. 14, 2010.

Office Action for U.S. Appl. No. 11/773,250 dated Dec. 13, 2010.

Bergquist, A.J. et al., "Motor unit recruitment when neuromuscular electrical stimulation is applied over a nerve trunk compared with a muscle belly: triceps surae," *J Appl Physiol* 110: 627-637, 2011.

Chesterton, L.S. et al., "Effects of TENS frequency, intensity and stimulation site parameter manipulation on pressure pain thresholds in healthy human subjects," Pain 106(1-2): 73-80, Nov. 2003.

Lammers, W.J.E.P. et al., "Origin and propagation of individual slow waves along the intact feline small intestine," *Exp Physiol* 93.3: 334-346, Dec. 2007.

Li, S. et al., "Cellular effects of gastric electrical stimulation on antral smooth muscle cells in rats," *Am J Physiol Regul Integr Comp Physiol* 298: R1580-R1587, 2010.

Lin, Z.Y. et al., "Effects of pacing parameters on entrainment of gastric slow waves in patients with gastroparesis," *Am J Physiol Gastrointest Liver Physiol* 274:G186-G191, 1998.

McCallum, R.W. et al., "Gastric Pacing Improves Emptying and Symptoms in Patients With Gastroparesis," Gastroenterology 1998; 114: 456-461.

O'Grady, G. et al., "Origin and propagation of human gastric slow-wave activity defined by high-resolution mapping," *Am J Physiol Gastrointest Liver Physiol* 299:G585-G592, 2010.

Palmer, S.T. et al., "Alteration of interferential current and transcutaneous electrical nerve stimulation frequency: effects on nerve excitation," Archives of Physical Medicine & Rehabilitation 80(9): 1065-71, Sep. 1999.

Weeks, E.S. et al., "Mucosal Temporary Gastric Stimulation for Patients with Symptoms of Gastroparesis: Proximal vs. Distal Leads Stimulation," Gastroenterology, vol. 140, Issue 5, Supplement 1, p. S-378, May 2011.

* cited by examiner

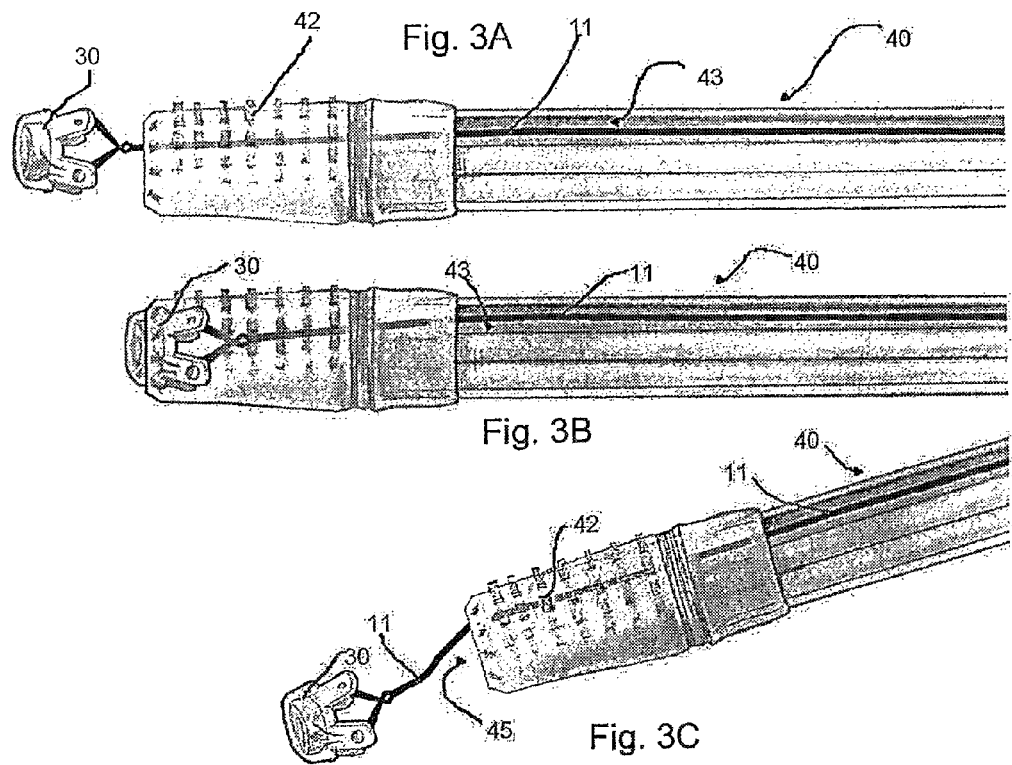
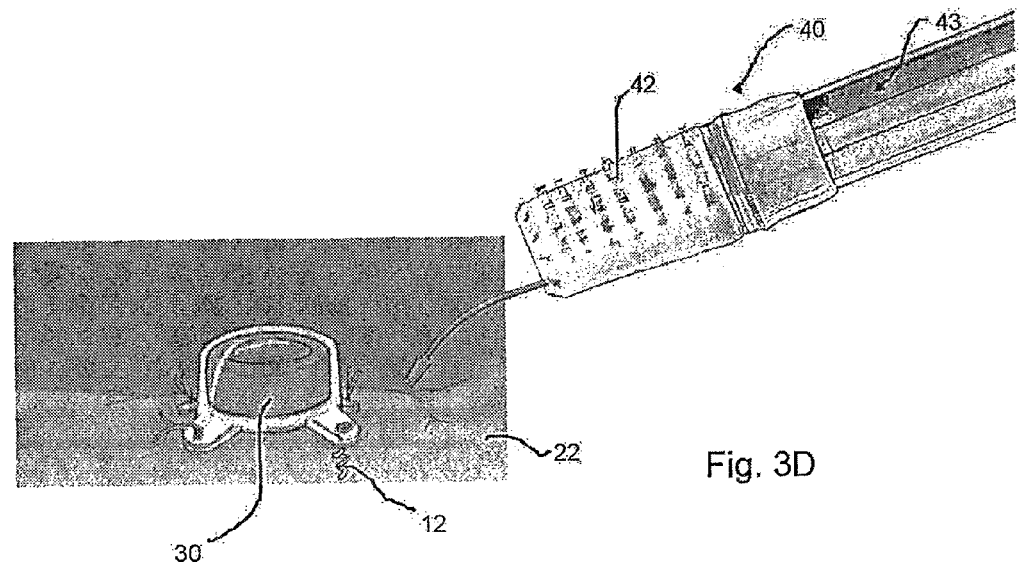

PRIOR ART

Algorithm for GES symptom improvement. SX=symptoms, mA=milliAmps, HZ=Hertz, GES=gastric electrical stimulation.

GASTROINTESTINAL ELECTRICAL STIMULATION DEVICE AND METHOD FOR TREATING GASTROINTESTINAL DISORDERS

CROSS REFERENCE TO RELATED APPLICATIONS

This is a continuation-in-part of U.S. patent application Ser. No. 11/773,250, filed Jul. 3, 2007; which claims priority to both U.S. Provisional Application Ser. No. 60/779,893, filed Mar. 7, 2006; and U.S. Provisional Application Ser. No. 60/802,150, filed May 19, 2006; all herein incorporated by reference.

FIELD OF THE INVENTION

The present invention relates generally to the field of treating and preventing gastrointestinal disorders. More specifically, the present invention relates to a novel device and method for use in the treatment of stomach and gastrointestinal disorders, including gastroparesis, nausea and vomiting, using electrical stimulation of the gastrointestinal ("GI") tract, as well as a method for screening candidates for treatment using electrical stimulation.

BACKGROUND OF THE INVENTION

A relatively new approach includes the use of devices for electrical stimulation. Electrical stimulation of the GI tract has previously been used to treat disorders, such as traditional gastroparesis and obesity. The treatment works, in part, by effecting one's natural gastric electrical activity, although other mechanisms, including ones effecting the autonomic nervous system, may be involved.

Electromechanical control of the GI tract depends on an interplay between background gastric electrical activity, often referred to as electrical control activity ("ECA") that occurs continuously, and the periodic occurrence of mechanical activity called electrical response activity ("ERA").

Two prior types of electrical stimulation are used in the GI tract. A first type of electrical stimulation in the GI tract, referred to as gastric electrical stimulation (or GI pacing) involves frequencies similar to those found physiologically, and uses higher energies, sometimes called: low-frequency and high-energy; long-pulse (a misnomer of the pulse width). This application remains experimental, in part due to the need for relatively large amounts of energy to be delivered to the GI tract, thus limiting permanent battery implementation, although several modifications to reduce energy use have been proposed.

A second type of electrical stimulation of the GI tract involves higher than physiological frequencies and much lower (by experimental numbers) energies sometimes called: high-frequency and low-energy; short-pulse (due to narrower pulse width) gastric electrical stimulation (GES), also known as gastric neuromodulation. This therapy, as a surgically implantable device in the gastric serosa, was approved by the FDA as a humanitarian use device for gastroparesis in 2000.

Gastroparesis, a disorder of gastric motility, broadly defined as delayed gastric emptying, can be acute or chronic. Symptoms of gastroparesis include early satiety, nausea, vomiting, dehydration, abdominal pain and nutritional compromise.[1] It may be attributed to impaired motor activity and/or impaired myoelectrical activity.[2] Gastric slow waves, which are necessary for contractions and normal gastric motility to occur, may have abnormal frequencies or amplitudes, resulting in gastric myoelectrical abnormalities. However, many patients with the symptoms of gastroparesis either have non-delayed emptying, which may or may not be defined as abnormal gastric emptying by other criteria, or have underlying diseases or disorders that do not qualify them for the current surgically implanted HUD device, and there has existed no way of seeing which patients might benefit from this type of therapy.

Management of drug refractory gastroparesis, as well as other disorders that involve chronic nausea and/or vomiting, is a challenge for both clinicians and patients. The prior art method of gastric electrical stimulation (GES), using a permanently implanted device, has been shown to be effective treatment in both randomized place controlled and long-term therapy in drug-refractory gastroparesis.[9,10] However, placement of a permanent GES device requires an elective surgical procedure and currently no non-invasive test is available to predict response to a permanent GES device.

The prior therapy of gastroparesis relies on dietary modifications that reduce meal size, and the administration of medications which enhance gastric contractility, thus accelerating gastric emptying. Agents with gastrokinetic effects include cisapride, metoclopramide, erythromycin and domperidone. Antiemetic agents such as promethazine and ondansetron may also help patients in decreasing symptoms of nausea and vomiting.[3,4,5] A number of patients with impaired gastric emptying report no appreciable symptom relief with prokinetic therapy and are classified as drug refractory.[6,7]

High frequency, low energy GES has shown efficacy for the treatment of drug refractory gastroparesis.[8,9,10] However, the prior art placement of a GES device usually requires surgery, as no current non-invasive test is predictive of response to it.

SUMMARY OF THE INVENTION

The present invention is directed to a novel method and device directed at using GES via mucosal internal/intestinal neural stimulation therapy ("MINT") to treat gastrointestinal disorders, including gastroparesis, nausea and vomiting, as well as disorders anywhere in the GI tract. The specific disorders may vary by their location, but the basic principles of measurement of the mucosal EGG, its analysis, and then a directed therapy, are the same in any location. Advantageously, the present method of GES is implemented by measuring mucosal EGG activity, analyzing the EGG signal, and then optimizing the electrical stimulation to be applied.

The present invention, in one form, is directed to a method for treating disorders relating to abnormal gastric electrical activity in a patient via the mucosal route and, especially, via endoscopic visualization. The method includes determining frequency and amplitude of natural gastric electrical activity in the patient; calculating a frequency to amplitude ratio; and administering electrical stimulation to the gastrointestinal tract of the patient based on the frequency to amplitude ratio, to thereby normalize the gastric electrical activity in the patient, and thus improve the patient's specific symptoms.

Advantageously, the electrical stimulation is administered by applying electrical current having a pulse width often in the range of 200 microseconds to 5 milliseconds, current typically in the range of 5 to 20 m Amps with an amplitude typically in the range of 5 to 10 Volts, a burst frequency often in the range of 10-100 Hz, and a frequency of burst often in the range of 5 to 50 bursts per minute, but the specific parameters are often determined by the components of the FAR measured by the mucosal EGG.

The present invention, in another form, relates to a method for treating gastrointestinal disorders relating to abnormal gastric electrical activity as a manifestation of disordered Enteric Nervous System (ENS) and/or abnormal Autonomic Nervous System (ANS) activity in a patient. The method includes determining frequency and amplitude of natural gastric electrical activity in the patient; calculating a frequency to amplitude ratio; and administering electrical stimulation to the gastrointestinal tract of the patient based on the frequency to amplitude ratio, to thereby treat the gastrointestinal disorders.

Advantageously, this mucosal GI method is applicable for the treatment of the above mentioned gastrointestinal disorders, including gastroparesis, dyspepsia, gastro-esophageal reflux and nausea/vomiting of any etiology, along with disorders such as hyperemesis gravidarum of pregnancy, acute and chronic pancreatitis and other pancreato-biliary disorders, including biliary dyskinesia; nausea/vomiting of chemotherapy and/or related to other cancer therapies; rapid and other disordered gastric emptying; metabolic disorders including diabetes; bacterial overgrowth and small bowel dysmotility; constipation, diarrhea and pelvic floor disorders; autonomic disorders; post-transplantation disorders; other post-surgical disorders; and nutritional disorders related to inability to maintain adequate weight. Also included are classic eating disorders, such as anorexia nervosa or bulimia nervosa and the inability to lose weight.

The present invention, in another form, is directed to a method for treating gastrointestinal disorders relating to abnormal gastric electrical activity in a patient. The method includes implanting, endoscopically, an electrode in the mucosal lining of the gastrointestinal tract of the patient; and administering electrical stimulation through the electrode to the gastrointestinal tract at an effective current, to thereby treat the gastrointestinal disorders. In one advantageous form, the method further includes measuring frequency and amplitude of natural gastric electrical activity in the patient using the electrode; and calculating a frequency to amplitude ratio.

The present method, in another form, relates to selecting advantageous candidates for gastric electrical stimulation. The method includes determining frequency and amplitude of natural gastric electrical activity in the patient, calculating a frequency to amplitude ratio, identifying patients as potential candidates for mucosal or other gastric electrical stimulation as individuals having a frequency to amplitude ratio generally in the range of 1-100, and treating the identified patients with gastric electrical stimulation to thereby treat the disorder related to gastric electrical activity.

Advantageously, the present invention uses mucosal electrogastrogram ("EGG") and analysis of frequency amplitude ratio ("FAR") determined from measuring the frequency and amplitude of electrical activity from the mucosal EGG of a patient's natural gastric electrical activity, to normalize gastric electrical [current] activity. The present method can be used for other disorders relating to abnormal gastric electrical current using neural modulation. This neural modulation can be effectuated using endoscopy.

The FAR analysis, in one advantageous process, is analyzed by a signal averaging technique. In this technique, one uses the average frequency and average amplitude in order to calculate the FAR. From data collected, FAR is correlated to normal physiological electrical status, as discussed in detail below in Examples XII and XIII.

Electrical current from the neural modulation device can be provided to the gastrointestinal tract using various different methods. Advantageously, stimulation is provided via mucosal internal/intestinal neural stimulation therapy ("MINT"). However, depending on the treatment, other delivery methods, such as serosally attached internal/intestinal neural stimulation therapy ("SAINT") and percutaneous internal/intestinal neural stimulation therapy ("PINT"), can be used.

As previously noted, advantageously, electrical stimulation is provided by the present method by inserting electrodes/terminals into mucosal tissue of the GI tract using an endoscopic visualization and/or delivery approach. An EGG is performed using the electrodes. The electrical terminals are then connected to a neural modulation device which may be the same device or a different device from the one which is used for producing the EGG. Accordingly, the same electrodes used for the EGG can be used for delivering electrical simulation. Delivery of a desired electrical stimulation is provided using a novel frequency amplitude ratio ("FAR") based on an analysis of a patient's existing gastrointestinal electrical activity, as determined from the EGG. One advantageous feature, in accordance with the present invention, is the ability to provide relatively non-invasive electrical stimulation of the entire GI tract.

The present method may be used for other disorders having a nexus to gastrointestinal electrical activity, including but not limited to the following: mucosal diagnosis and related therapy of gastroparesis and dyspepsia, gastro-esophageal reflux, nausea/vomiting of any etiology, including hyperemesis of pregnancy, acute and chronic pancreatitis and other pancreato-biliary disorders, including biliary dyskinesia; nausea/vomiting of chemotherapy and/or other cancer related therapies with resultant GI debilitation, including for palliative care, rapid and other disordered gastric emptying, diabetes and other metabolic disorders, bacterial overgrowth and small bowel dysmotility, constipation, diarrhea and pelvic floor disorders; autonomic disorders; transplantation related GI disorders; other post-surgical disorders; and nutritional disorders with inability to maintain enteral intake and/or maintain adequate weight, as well as classic eating disorders and the inability to lose weight in some patients.

Various forms of the present invention relate to novel methods of accessing the enteric nervous system for endoscopic measurements and electric stimulation. Differing forms of the present invention further comprise the use of novel electrodes and a novel process of acquiring and analyzing electrical data using the mucosal surface.

The present invention, in another form, relates to a device for treating disorders relating to abnormal gastrointestinal electrical activity in a patient. The device comprises an electrode for insertion into the gastrointestinal tract of patient for measuring gastrointestinal electrical activity and for administering electrical stimulation; and an endoscopically insertable neural modulation device. The neural modulation device operatively associated with the electrode for delivering an electrical impulse to the patient.

An example of an electrode, in accordance with the present invention, includes one that is implantable into a layer of the stomach, such as the sub-mucosal layer, to stimulate the nerves therein. The electrode is implanted using an endoscope. One advantageous further feature of the present method is that it allows one to measure and then stimulate the enteric nervous system without the risks and drawbacks of major surgery.

Additionally, the present invention allows access to the enteric nervous system from the mucosal surface and the sub-mucosal plexus, allowing endoscope placement of electrodes. This is in contrast to prior methods of GES which required abdominal surgery.

BRIEF DESCRIPTION OF THE FIGURES

FIGS. 2A-2D are schematic views showing various ways for insertion of an electrode for use during GES, according to additional aspects of the present invention, wherein FIG. 2A shows insertion and attachment using a magnet, FIG. 2B shows attachment using a needle, FIG. 2C shows attachment using a clip, and FIG. 2D shows attaching using sutures;

FIGS. 3A-3D show insertion of a GES device, in which FIG. 3A shows an electrode insertion tool and a neural modulation device, after attachment in accordance with the present invention, FIGS. 3B and 3C show the insertion tool during insertion, and FIG. 3D shows a partial view of the device inserted into the tissue of a patient, in accordance with the present invention;

DETAILED DESCRIPTION

Figure 1:
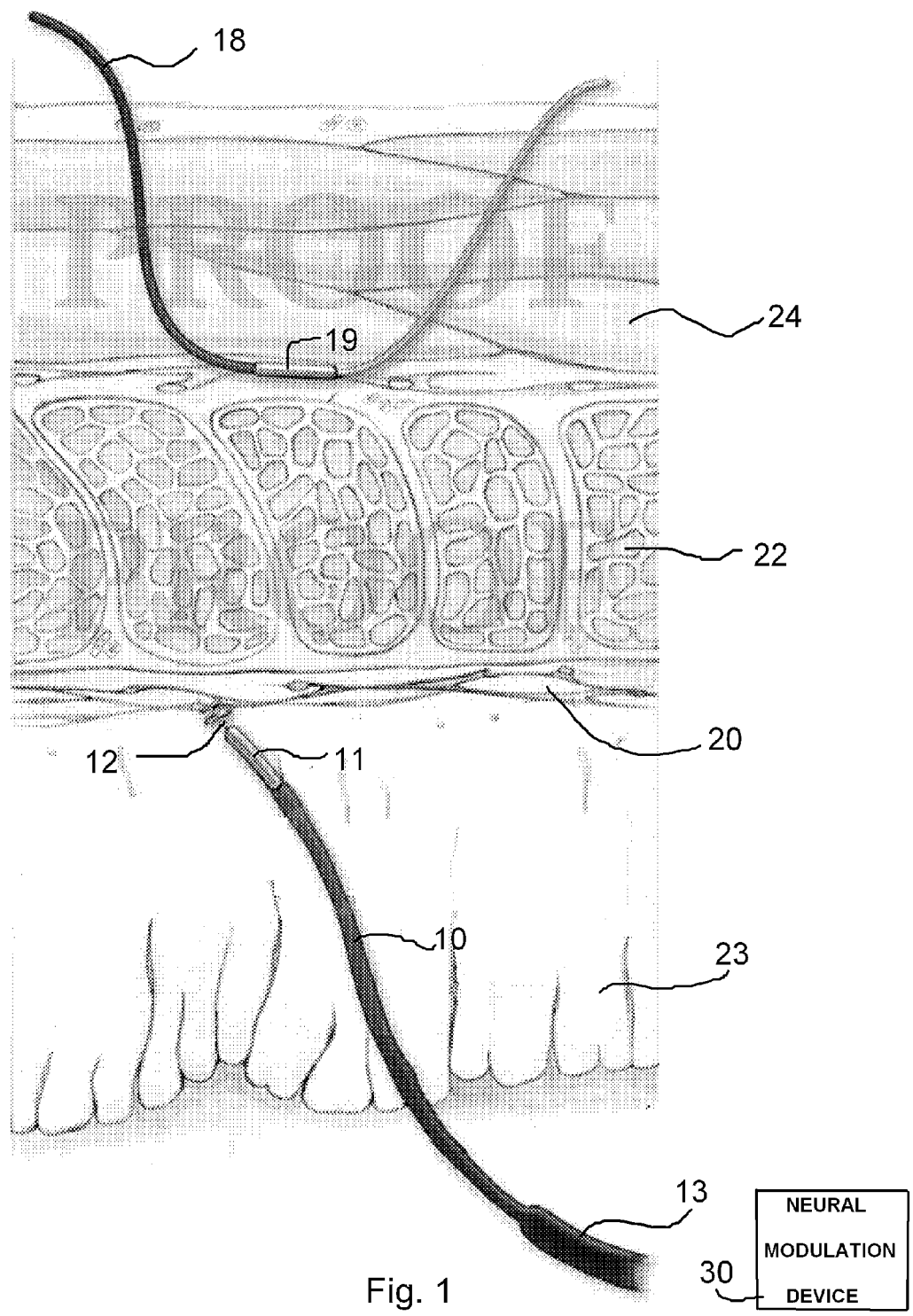
FIG. 1 shows insertion of an electrode in the mucosal surface of a patient's GI tract, for use in measurement of the mucosal EGG and then mucosal gastric electrical stimulation, in accordance with the present invention.

The present invention is directed to providing mucosal temporary gastric electrical stimulation ("tGES") to treat gastrointestinal disorders, including gastroparesis, nausea and vomiting in the form of mucosal electrical stimulation of the GI tract. Using the present method one can achieve an effective treatment of gastrointestinal disorders, especially disorders relating to abnormal gastric electrical activity in a patient, which include, but not limited to, gastroparesis, dyspepsia, gastro-esophageal reflux and nausea/vomiting of any etiology, along with disorders such as hyperemesis gravidarum of pregnancy, acute and chronic pancreatitis and other pancreato-biliary disorders, including biliary dyskinesia; nausea/vomiting of chemotherapy and/or related to other cancer therapies; rapid and other disordered gastric emptying; metabolic disorders including diabetes; bacterial overgrowth and small bowel dysmotility; constipation, diarrhea and pelvic floor disorders; autonomic disorders; post-transplantation disorders; other post-surgical disorders; and nutritional disorders related to inability to maintain adequate weight. Also included are classic eating disorders, such as anorexia nervosa or bulimia nervosa.

Advantageously, the present method can be implemented by implanting, endoscopically, an electrode in the mucosal lining of the gastrointestinal tract of a patient. Using the electrode, one can perform an EGG and from the EGG measure frequency and amplitude of naturally occurring gastric electrical activity in the patient, as well as calculate a frequency to amplitude ratio ("FAR"). From the FAR, one can assess whether the patient is a good candidate for GES and can adjust GES parameters accordingly, to provide the requisite electrical stimulation to treat the patient's disorder. Ideal candidates for the present GES will have a FAR in the range of 1 to 100 cycles per minute (CPM)/millivolt (MV). Subsequently, electrical stimulation is delivered through the electrode to the gastrointestinal tract of the patient at an effective current, to thereby treat the gastrointestinal disorders.

Typically, the electrical stimulation is administered by applying electrical current having a pulse width typically in the range of 200 microseconds ("μsec.") to 5 milliseconds ("msec."), in the range of 5 to 20 mAmps, in the range of 5 to 10 volts, a frequency of bursts typically in the range of 5 to 50 bursts per minute, and a burst frequency in the range of 10-100 Hz. However, these parameters are determined by the compounds of the FAR measured by the mucosal EGG.

For example, it will be clear to one skilled in the art that certain patient groups, such as post-surgical patients, require more energy. Since the mEGG helps correlate with neuromuscular status, the mEGG and, especially, the FAR can be used to calculate specific stimulation parameters.

The preferred electrical stimulation, in accordance with the present invention, is that amount and form, e.g. current, voltage, frequency, etc., which will be effective in treating gastrointestinal disorders, and, ideally, will restore normal physiological gastrointestinal electrical activity, to thereby treat the gastrointestinal disorders. One would readily recognize that this amount will vary greatly depending on the nature and extent of the patient's natural gastrointestinal electrical activity, the extent and type of gastrointestinal disorder to be treated, and the condition of a patient. An "effective amount," in accordance with the invention, is intended to mean a non-harmful, but sufficient delivery amount of electrical stimulation, such that the desired prophylactic or therapeutic effect is produced. Thus, the exact amount of electrical stimulation required will vary from subject to subject, depending on the age, and general condition of the subject, the severity of the condition being treated, mode of electrical stimulation administration, and the like. Similarly, the dosing regimen should also be adjusted to suit the individual to whom the composition is administered and will once again vary with age, weight, metabolism, etc. of the individual. Accordingly, the "effective amount" of any particular treatment will vary based on the particular circumstances, and an appropriate effective amount may be determined in each case of application by one of ordinary skill in the art using only routine experimentation.

As noted, advantageously, the present invention uses mucosal electrogastrogram ("EGG") and analysis of frequency amplitude ratio ("FAR") determined from measuring the frequency and amplitude of electrical activity from the mucosal EGG of a patient's natural gastric electrical activity, to normalize gastric electrical [current] activity. The present method can be used for other disorders relating to abnormal gastric electrical current using neural modulation. This neural modulation can be effectuated using endoscopy via an endoscopic approach, as described above and discussed in greater detail below.

In one form, providing GES produces a rapid and marked improvement in patients with intractable symptomatic gastroparesis. Various forms of the present method can be performed on patients who are either too ill to undergo open surgical procedure or waiting for permanent gastric electrical stimulation device placement due to reimbursement issues. Mucosal measurements allow a minimally-invasive way to determine which patients may respond to GES.

Advantageously, the present method uses high frequency, low energy gastric electrical stimulation. While not being bound by one particular theory, it is believed that the use of high frequency, low energy may work via neural stimulation, and thus may have a different mechanism than low frequency, high energy gastric pacing.[13, 14] Energy calculated, in particular, is much lower with GES than gastric pacing.[9, 10]

Referring now to the figures, FIGS. 1-3, relate to the implementation of the present GES using practiced MINT, in accordance with the present invention. Referring specifically to FIG. 1, an endoscopic mucosal electrode 10 is placed into the gastric mucosa 20, near the submucosal plexus 22, which is adjacent the inner circular muscle 23 for MINT. Electrode 10 has a mucosal electrode end 11 with insertion tip 12 which is in the form of a conducting corkscrew, and an end 13, opposite the insertion tip 12. The insertion tip 12 is inserted directly into the gastric mucosa 20 at the submucosal plexus 22.

In an alternative insertion method, although depicted also in FIG. 1, electrode 18 has a lead 19, which can be inserted through the serosal or outside of the gut into the muscle layers of the inner circular muscle 23 and the longitudinal muscle 24 for SAINT.

Referring back to MINT insertion, the electrode end 13 can be connected to any appropriate device for providing an EGG, which may or may not be the same device which will be used to deliver electrical stimulation to the gastric mucosa 20, such as neural modulation device 30, shown schematically in FIGS. 1 and 2A-2D.

Referring now specifically to FIGS. 2A-2D, alternative attachment methods to the one shown in FIG. 1 (i.e. attachment via a corkscrew shaped electrode, namely insertion tip 12), are illustrated. Specifically referring to FIG. 2A, electrode 110 has a magnetic end 111. A magnet 140 is placed externally at location 142 adjacent the gastrointestinal tract and, in particular, extending to the mucosa, so that neural modulation device 130 can deliver electrical stimulation to gastric mucosa 120. The electrode 110 is held in place using magnetic attraction between external magnet 140 and the magnetic tip 111.

Figure 2A:
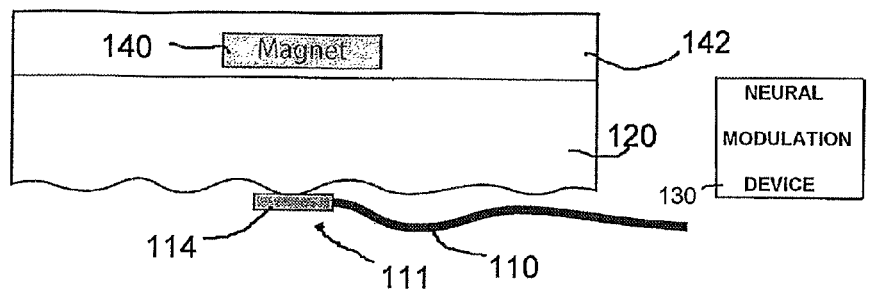
Figure 2B:
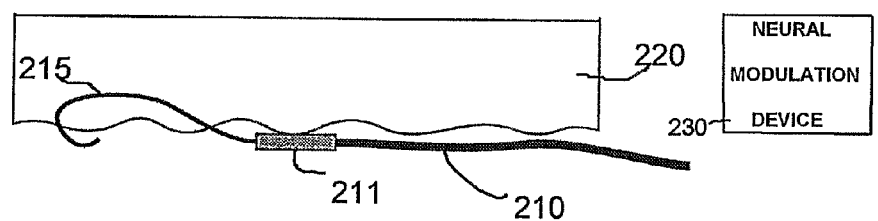

Referring to FIG. 2B, neural modulation device 230 is held in place to deliver electrical stimulation to gastric mucosa 220 through electrode end 211 using a needle 215.

Figure 2C:
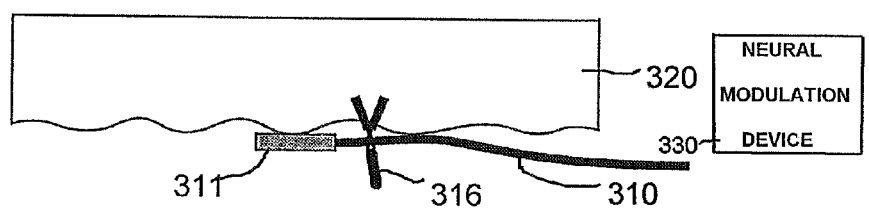

Referring to FIG. 2C, electrode 310 uses clip 316 to hold neural modulation device 330 in place to deliver electrical stimulation to gastric mucosa 320 via electrode end 311.

Figure 2D:
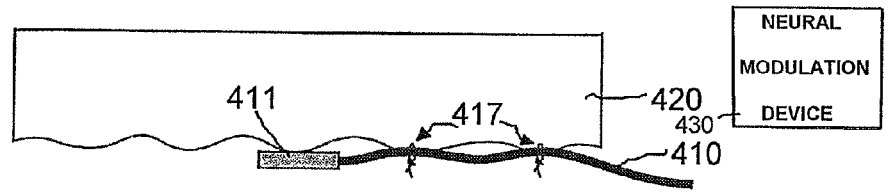

Referring to FIG. 2D, electrode 410 is sutured to the gastric mucosa 420 using a pair of sutures 417 which holds the electrode tip 411 in close proximity and abutting the gastric mucosa 420, for delivering electrical stimulation from neural modulation device 430 to the gastric mucosa 420 via electrode end 411.

Referring generally to FIGS. 3A-3D, along with FIGS. 1 and 2A-2D, an endoscope 40 is used for the insertion of the endoscopic electrodes, such as 10, 110, 210, 310, 410 (FIGS. 3A-3D depicting electrode 10) for providing an EGG and subsequent GES. As shown in FIG. 3A, device 30 is initially attached to the end of electrode 10. Endoscope 40 has an endoscope outer sheath 42, which accommodates the device 30. Endoscope 40 provides for the advancement of both the electrode 10 and device 30 inserted therein. Specifically, the electrode 10 is carried in the endoscope's biopsy channel 43, which accommodates the device 30 and electrode 10.

Referring to FIG. 3B, endoscope 40 is used to advance the device 30 and electrode 10 to the gastric mucosa 20 and for subsequent screwing of the insertion tip 12 into the gastric mucosa 20, as shown in FIG. 3D. Endoscope 40 can also be used to attach electrodes 110, 210, 310, 410, as described and depicted in FIGS. 2A-2D, respectively, for magnet 114 attachment, insertion needle 215, using clips 316 or sutures 417, respectively. Further, endoscope 40 provides visualization of the attachment by the aforementioned means and mechanisms through the usual visualization channel common in endoscopes known currently in the art, such as visualization channel 45.

Referring specifically to FIG. 3A, after the electrode, e.g., electrode 10, has been implanted anywhere on the gastrointestinal mucosa, baseline gastric electrical activity is measured using the electrodes 10 and any appropriate device which measures the patient's baseline or existing, natural gastrointestinal electrical activity. As noted above, the appropriate device for measuring baseline or existing natural gastrointestinal electrical activity can be any device currently used for making such measurements. Alternatively, as noted above, a neural modulation device 30 can be used which can optionally have the functionality of being able to measure gastrointestinal electrical activity.

Based on the electrical activity measured, one can confirm that the electrode 10 has been inserted correctly and can then determine the type of stimulation necessary, i.e. frequency and amplitude of the electrical stimulation needed, in order to provide the requisite treatment, i.e. gastrointestinal disorders, including those identified herein and linked to abnormal gastrointestinal electrical activity. While the MINT method is a preferred procedure for electrode insertion, other methods may be adapted to place an electrode and/or device mucosally using an endoscope.

If another device other neural modulation device 30 is used for the EGG, subsequently, the electrodes are removed from that EGG device and then connected to the neural modulation device 30 which provides artificial electrical stimulation to the gastrointestinal tract.

It should be noted that there are advantages to having the neural modulation device 30 produce the EGG. One advantage of the neural modulation device 30 being able to measure gastrointestinal electrical activity is that device 30 can then implement/incorporate a feedback mechanism in which gastrointestinal electrical activity can be monitored and the electric current delivered through electrode 10 can be altered and adjusted to optimize the amount of current delivered to the patient through electrode 10, based on EGG readings.

As will be discussed in much further detail below, the present method of GES can be used as a treatment for disorders which are now known to be linked to abnormal GI electrical activity. These disorders include nausea/vomiting relating to motion sickness associated with autonomic nervous system changes and chemotherapy nausea/vomiting associated with gastric/enteric nervous system changes. Further, the present tGES measures the enteric nervous system and can easily be applied to chemotherapy nausea/vomiting, including gastroparesis, dyspepsia, gastro-esophageal reflux and nausea/vomiting of any etiology, along with disorders such as hyperemesis gravidarum of pregnancy, acute and chronic pancreatitis and other pancreato-biliary disorders, including biliary dyskinesia; nausea/vomiting of chemotherapy and/or related to other cancer therapies; rapid and other disordered gastric emptying; metabolic disorders including diabetes; bacterial overgrowth and small bowel dysmotility; constipation, diarrhea and pelvic floor disorders; autonomic disorders; post-transplantation disorders; other post-surgical disorders; and nutritional disorders related to inability to maintain adequate weight. Also included are classic eating disorders, such as anorexia nervosa or bulimia nervosa.

In addition, the present method can be used to treat other causes of nausea and vomiting, including any etiology. Further, the method can be used anywhere in the GI tract to access the enteric nervous system to aid in the amelioration of symptoms or improve mortality, such as small bowel, biliary pancreatic disorders and colonic conditions.

One particularly advantageous administration of gastric electrical stimulation is in the form of optimizing the frequency amplitude ratio of a patient's gastric electric activity. Advantageously, the GES should be provided at appropriate parameters, levels of frequency, amplitude, burst frequency and frequency of burst to normalize gastroelectrical activity, thereby achieving a physiologically normal electrical activity, as discussed above.

In addition, prior to electrical stimulation, baseline measurements are taken for a patient's natural gastric electrical activity via electrode 10, including the electrical frequency, and amplitude of the electrical activity. Based on that ratio of frequency to amplitude (FAR), one can determine who will benefit from the present GES. In particular, FAR numbers in the ranges of 1 to 100 cycles per minute (cpm)/millivolts (mV) are likely to see positive results from the present GES.

Figure 11:
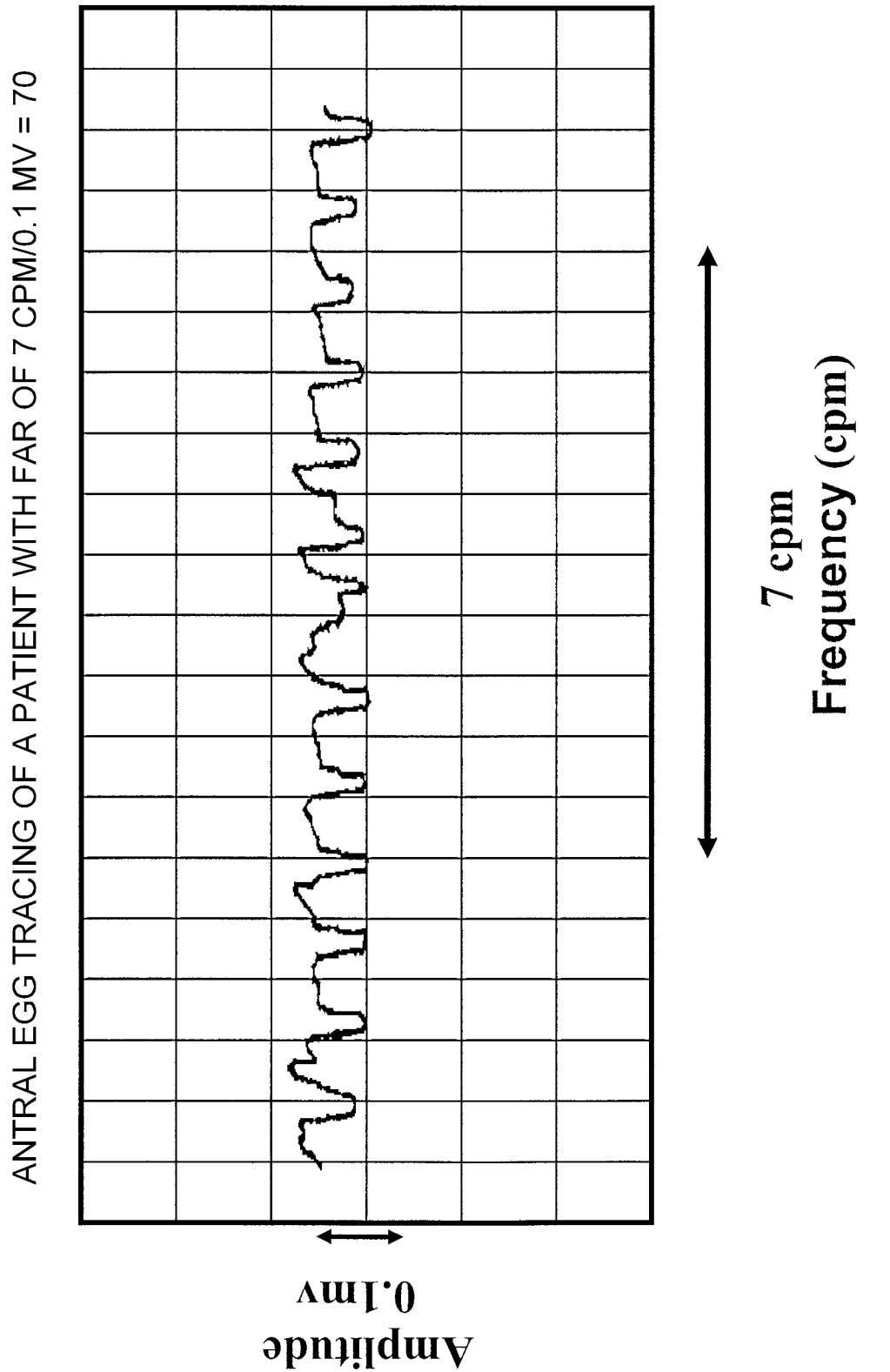
FIG. 11 is a graph plotting amplitude vs. frequency of an antral EGG tracing of a patient with a FAR of 7 cycles per minute (CPM)/0.1 millivolt (mV)=70 cpm/mV, in accordance with the present invention.

Referring now to FIG. 11, the graph relates amplitude vs. frequency of an antral EGG tracing of a patient with a FAR of 7 cycles per minute (cpm/0.1 millivolts (mV) (i.e. 70 cpm/mV).

The present GES is distinguishable over prior known methods which use gastric electrical stimulation, in that the present method the electrodes are implanted using an endoscope, wherein the electrodes provide for modulation of gastric function to improve symptoms or function, to thereby restore normal GI function. Unique in the present method is application and insertion of an electrode using an endoscope, and using the electrode to measure electrical activity of the GI tract as a way to optimize the method depending on the physiology of the patient, including the disorder to treat.

A further unique aspect of the present method is the use of a feedback system in which the present method measures initial natural, baseline gastric electrical activity, applies electrical stimulation, takes a second measurement of electrical activity, adjusts the electrical stimulation and repeats this process in order to achieve a desired gastric electrical activity.

The electrodes can be applied anywhere in the GI tract from the mucosal side, not just to the stomach, which includes areas such as the small bowel or pancreatic area or the colon.

The following examples are presented purely for exemplary purposes, and are not intended to limit the scope of the invention.

Example I

Example I includes two phases. Phase I is an example of a short-term study of the devices and methods in accordance of the present invention, and Phase II is a corresponding long-term study.

The Phase I (Short-term) study includes 20 patients (6 male, 14 female, mean age of 43 years) with underlying disorders (8 Idiopathic, 5 Diabetes Mellitus and 7 Post Surgical Gastroparesis).

The Phase II (Long-term) study includes 13 patients (4 male, 9 female, mean age of 43 years) with underlying disorders (7 Idiopathic, 2 Diabetes Mellitus, 4 Post Surgical Gastroparesis) who first underwent tGES placement followed by permanent GES device implantation.

In both phases, measures of symptom assessment and related parameters were performed. Vomiting frequency score (VFS) shows the number of vomiting episodes scaled on 0-4, (0 being absent to 4 being extremely frequent, as >7/week). An average total symptom score (TSS) was recorded based on symptoms of abdominal pain, bloating/distention, nausea, vomiting and early satiety. Each symptom was rated as 0 to 10, none to severe, and the maximum score was 50. A gastric emptying test (GET) for liquids and solids was performed in patients before and after temporary gastric electrical stimulation (tGES).

In addition to TSS, VFS and GET results, measured electrode impedance and time to improve in days (>50% reduction in vomiting) were compared.

The electrode and device impedance in ohms ($Z=\Omega$) was determined using a Medtronic model 7432 programmer. A value for the average pulse charge energy and power was calculated using the measured impedance and the standardized parameters, i.e. frequency, amplitude (current), pulse width and the cycle ON and OFF time.

Gastric mucosal EMG (mEGG) can be recorded at any time during temporary stimulation from the stimulating electrodes. In this study, mEGG was recorded after attaching the stimulator electrodes, but before the tGES was begun. Cutaneous EGG can be recorded before, during or after stimulation.

Phase I (Short-term) study: Comparison of Endoscopic placement (ENDOstim) and PEG placement (PEGstim): 20 patients with drug refractory gastroparesis (GP) and tGES device placement received gastric electric stimulation electrodes placed either endoscopically (ENDOstim: n=6) or via PEG (PEGstim: n=14) as follows:

ENDOstim: Endoscopic Placement of GES Electrode

Using a standard 140 cm long EGD scope with a 7F-biopsy channel, an area as close as possible to the antral-body junction of the stomach is localized and a Medtronic 6414-200 temporary cardiac pacing lead is placed through the biopsy port. The 6414 temporary lead comes as an inner bipolar electrode pacing lead and an outer covering sheath. The outer sheath is only 120 cm long, so it does not come out at the other end of the biopsy port.

Figure 4A:
FIG. 4A is a photograph showing a prior art PEG placement using endoscopic visualization where a fetal scalp electrode is screwed into gastric mucosa through a PEG tract.
Figure 4B:
FIG. 4B is a photograph showing endoscopic placement of a gastric stimulator electrode through a biopsy electrode port.

The long inner lead is passed through the biopsy port and screwed into the stomach mucosa by clockwise corkscrew motion. The outer sheath is then removed, while keeping the inner lead in place (FIG. 4B).

The endoscope is withdrawn, while advancing the inner lead, so that it stays in position, being sure to leave some extra lead at least 10 cm in the stomach. It is helpful to keep the electrode from coiling excessively while being inserted, in order to facilitate clipping.

Figure 4C:
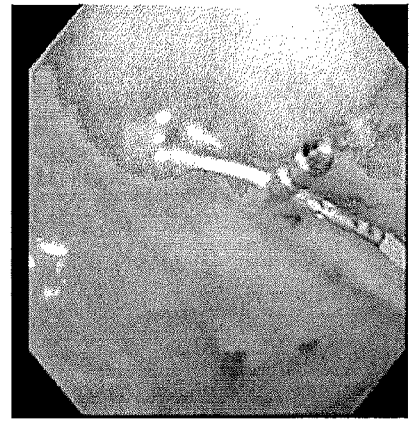
FIG. 4C is a photograph showing the electrode secured with clips, in accordance with the present invention.

The endoscope is reintroduced into the stomach. An Olympus endoscope clipping device is passed through the biopsy port and 3-5 clips are applied on the lead to hold it in place with the stomach wall. Placing at least one clip near the distal metallic part of the terminal part of the lead, as shown in FIG. 4C, is helpful to achieve desirable electrical impedance.

The lead is connected to a Medtronic external GES device, which is placed in the patient's shirt pocket, cardiac telemetry pouch or fanny pack, and the impedance is determined (desirable 400-800Ω).

GES device (Enterra®, Medtronic) is programmed, beginning with previously standardized parameters: Frequency=14 Hz, Amplitude=5 mA-10 mA, Pulse Width=330 µsec, Cycle ON=0.1-1.0 sec, Cycle OFF=5.0-4.0 sec. These parameters are used as a starting point, and may be modified for a given patient.

The ENDOstim electrodes remained in place until a repeat GET was performed after 2-3 days. The electrode was then removed manually by turning the electrodes counterclockwise and applying gentle pressure, which can be accomplished in an exam room.

PEGstim: PEG Placement of GES Electrode

Using a standard 140 cm long EGD scope to visualize the stomach, the PEG tube bumper and PEG tube are removed. A guide wire may be used for ease of electrode placement and to keep the PEG tract open.

Through the PEG tract, a fetal scalp electrode (Graphics Controls Corp., model ESE 1000 or equivalent) is introduced from outside the abdomen and screwed into the gastric mucosa using a clockwise corkscrew motion under direct endoscopic visualization. The lead is placed as close to the antral-body junction as possible (FIGS. 4B and 4C).

At least two leads are placed, keeping a distance of at least 1 cm between them. Due to the size and depth of these leads, an endoscopic clip is not necessary to maintain them in position. The leads are connected to the external GES device (Enterra®, Medtronic), the impedance is checked (desirable 400-800Ω) and the device is programmed to the parameters mentioned in ENDOstim below.

A smaller size PEG tube or a Foley catheter can be placed through the same tract to keep the tract patent. The electrode leads remain in the tract along side of the PEG tube or Foley catheter.

The PEGstim electrodes remain in place until a repeat GET in 2-3 days. Some patients wish to have the electrodes remain in place, often until time of permanent device implantation, and this was done in several patients.

Figure 5:
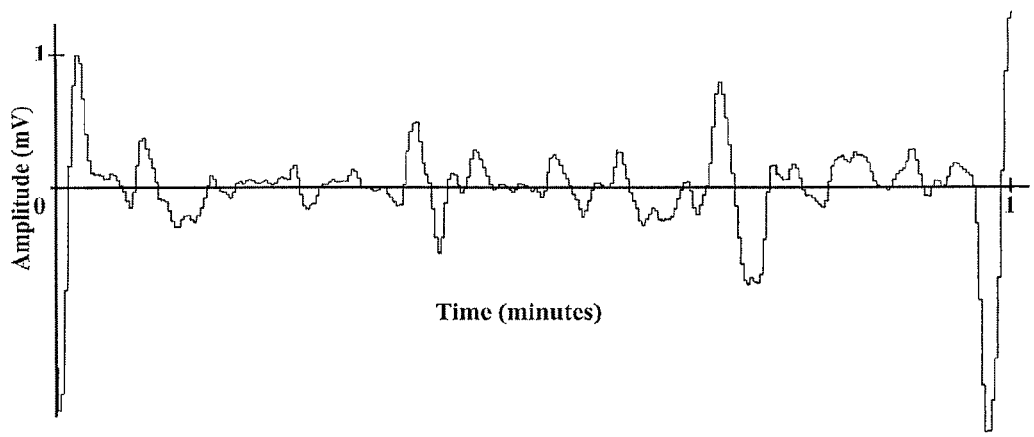
FIG. 5A is a graph showing mucosal gastric EGG.
FIG. 5B is a graph showing cutaneous EGG in the same patient, in which similar frequencies are observed in the EGGs of FIGS. 5A and 5B and a greater amplitude and a clearer signal is present in the mucosal EGG of FIG. 5A.
Figure 5:
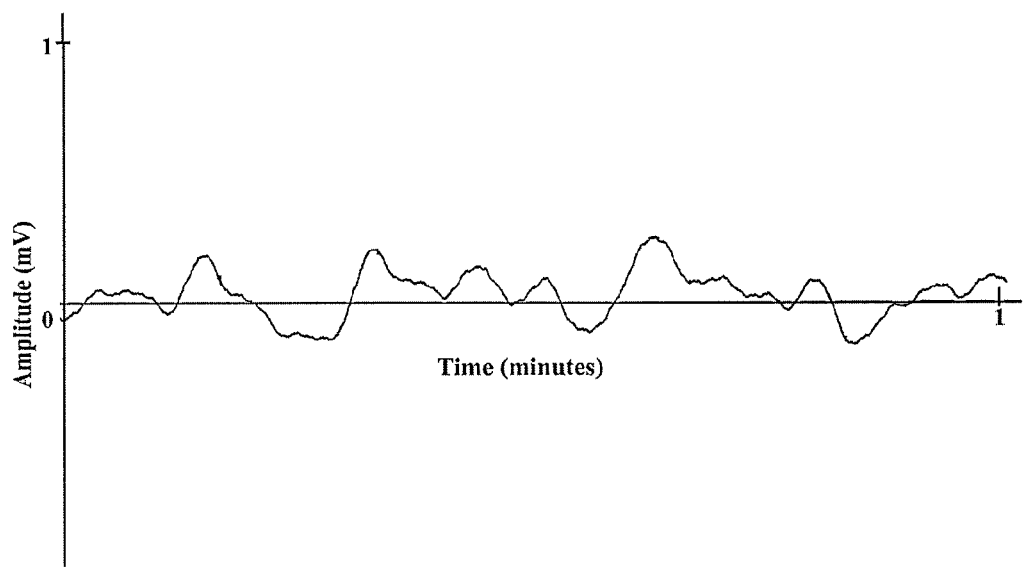

In either ENDO or PEG stimulation, IV glucagon (1 mg), given during the procedure, may decrease gastric motility and make placement easier, although glucagon can alter gastric electrical activity, making recordings less representative at baseline.[11] The VFS, TSS, days to symptom improvement, electrode impedance and GET were compared between the two group and for all patients as a group. An example of mucosal gastric EMG with temporary stimulation and cutaneous EGG, after permanent implant in one patient, are included as FIGS. 5A and 5B.

Phase II (Long-Term) Study: Comparison of Temporary with Permanent Gastric Electrical Stimulation.

To evaluate long term efficacy, tGES is compared with permanent gastric electrical stimulation in thirteen patients. Nine of the thirteen patients had permanent devices placed as part of a GEMS study group,[10] and four others had permanent devices placed as the result of FDA approved Humanitarian Use Device (HUD). VFS, TSS and GET for liquids and solids were compared between baseline and latest follow-up.

Statistical analysis: Paired students t test was used to compare baseline to follow up measures for both Phase I and Phase II studies, and unpaired t test was used to compare results between the two groups. Improvements in TSS between temporary and permanent phases were correlated for comparison. All data were presented as mean±SEM and the results were considered significant when p values were <0.05.

Results of Example I

Phase I Short-term Study: Comparing ENDOstim and PEGstim for Temporary Stimulation Temporary electrodes were placed as described above, and average time for endoscopic placement or PEG placement of electrodes was approximately 20 minutes. In Phase I, 17 of 20 patients (85%) improved in vomiting frequency score, and 19 of 20 (95%) improved in total symptom score. The patients as a group noted a rapid and sustained improvement in vomiting frequency score, improving from 3.5±0.3 at baseline to 1.2±0.4 after the device placement (p<0.05), an average improvement in VFS of 57.5±10.3%. VFS in the ENDOstim group (n=6) improved from 3.4±0.7 to 1.6±0.8 (p<0.05). VFS in the PEGstim group (n=14) improved from 3.6±0.3 to 1.2±0.4 (p<0.05).

The patients as a group noted a rapid and sustained improvement in total symptom score, improving from 37.8±2.4 at baseline to 19.4±3.0 after the device placement (p<0.05), an average improvement of 49.0±6.9%. The symptom reduction in the PEGstim and the ENDOstim groups were 56.3% and 32.1%, respectively. The number of days to improve (greater than 50% reduction in vomiting frequency) was similar in both groups (mean 2.71±0.63 days for ENDO vs. 2.3±0.6 days for PEG, p>0.05).

The average impedance (Z) recorded for patients in the ENDOstim group (Z=760Ω) was approximately twice that recorded in the PEGstim group (Z=376Ω) (p<0.05).

GET was performed on patients before and after tGES. The results for liquid GET improved from 65.7% to 58.3% (p<0.05) and from 42.2% to 37.0% (p>0.05) at 1 hour and 2 hours, respectively. The GET results, after solid meal ingestion, improved from 73.8% to 61.4% (p>0.05) and from 45.7% to 34.9% (p>0.05) at 2 hours and 4 hours, respectively.

Phase II Long-Term Study: Comparing Temporary Versus Permanent GES

The present invention compared the results of 13 patients who had temporary and then permanent GES devices placed via vomiting frequency score, total symptom score, percentage improvement, gastric emptying test for liquids and solids, of the two groups. In Phase II, 11 of 13 patients (85%) improved in vomiting frequency score and 12 of 13 patients (92%) improved in total symptom score, compared to baseline.

After permanent device placement, VFS improved from 3.5±0.3 at baseline to 1.6±0.5 (p<0.05). TSS improved from 37.5±3.0 to 18.0±3.9 (p<0.05). The results for liquid GET improved from 71.2% to 48.4% (p<0.05) and from 46.4% to 28.2% (p>0.05) at 1 hour and 2 hours, respectively. The GET results after solid meal ingestion improved from 74.6% to 56.2% (p>0.05) and from 36.9% to 24.2% (p>0.05) at 2 hours and 4 hours, respectively.

Figure 6:
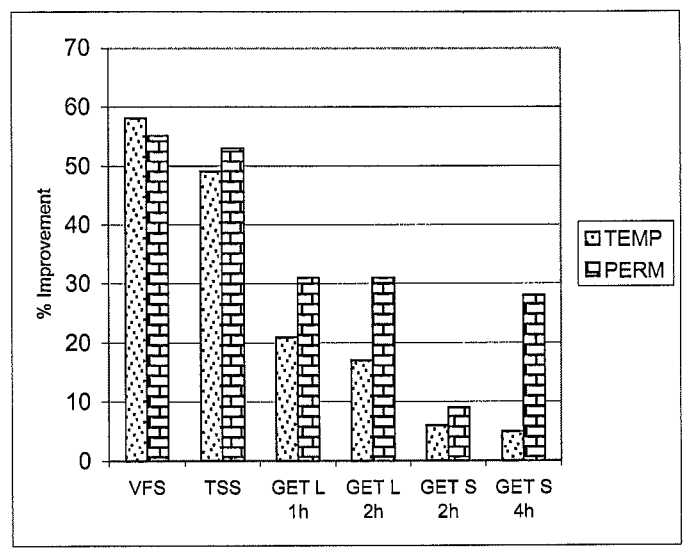
FIG. 6 is a graph comparing permanent GES and an embodiment of the present invention in terms of improvement (%) in symptoms.
Figure 7:
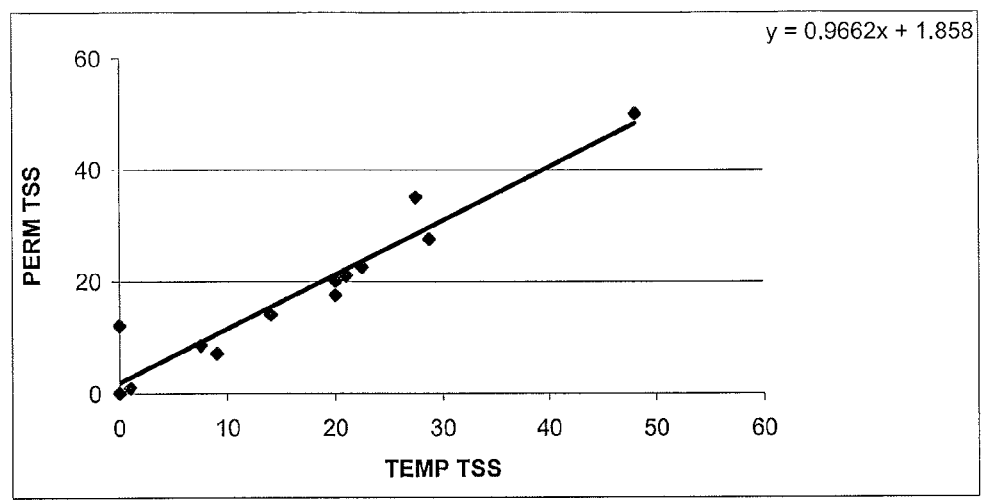
FIG. 7 is a graph showing GI total symptom score.
Figure 8:
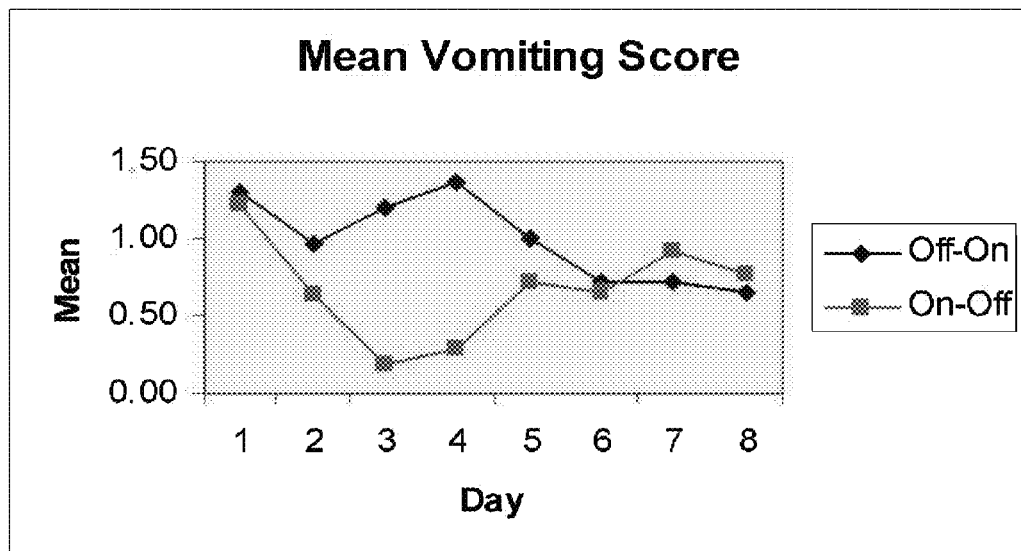
FIG. 8 is a graph relating to mean vomiting score in which the mean is plotted vs. days for OFF-ON and ON-OFF patients.
Figure 9:
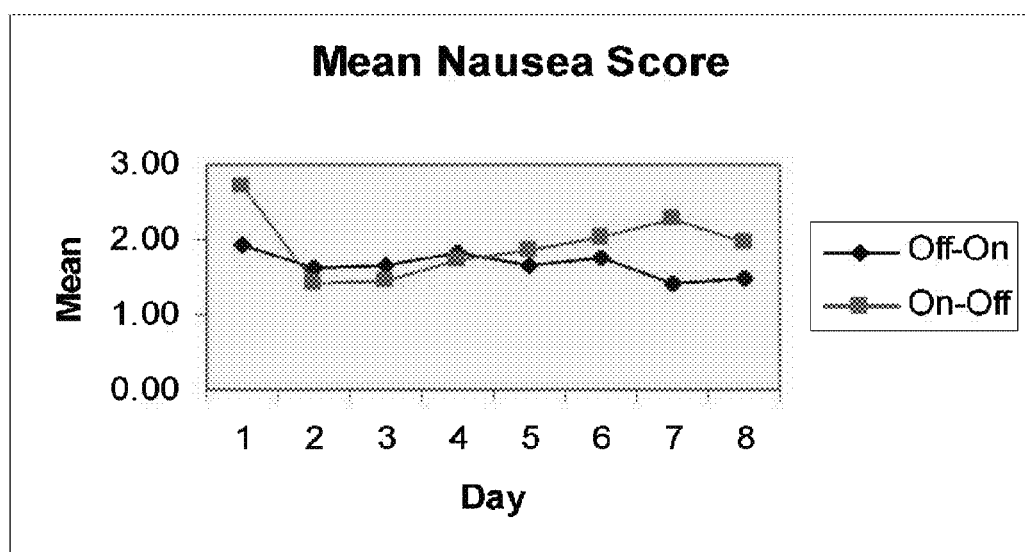
FIG. 9 is a graph relating to mean nausea score to days for OFF-ON and ON-OFF patients.
Figure 10:
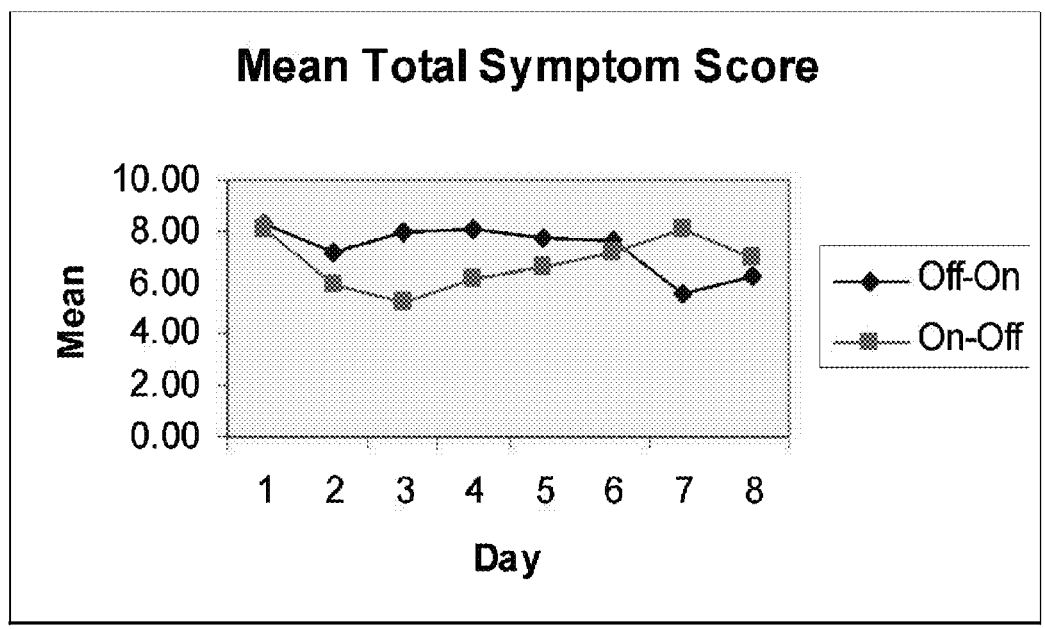
FIG. 10 is a graph relating to mean total symptom score, plotting mean vs. days for OFF-ON and ON-OFF patients, in accordance with the present method.

Results of the comparison between temporary and permanent GES are noted in Table 1 and the comparison of changes for temporary and permanent GES is shown in FIG. 6. FIG. 7 illustrates the comparison between GI Total Symptom Score for temporary and permanent device placement. The correlation of these two parameters was highly statistically significant (r=0.97).

TABLE 1

| | Symptoms Comparison - Temporary vs. Permanent GES (Mean ± SE) | | | | | | | | | | | |
|---|---|---|---|---|---|---|---|---|---|---|---|---|
| | | | | | GET Liquid 1 hr | | GET Liquid 2 hr | | GET Solid 2 hr | | GET Solid 4 hr | |
| | Before | After | Before | After | Before | After | Before | After | Before | After | Before | After |
| Temporary | 3.5 ± 0.3 | 1.2 ± 0.4* | 37.8 ± 2.3 | 19.4 ± 3.0* | 65.7 ± 8.0 | 58.3 ± 9.1* | 42.4 ± 7.7 | 37.0 ± 6.7 | 73.8 ± 5.9 | 61.4 ± 8.0 | 45.7 ± 9.7 | 34.9 ± 11 |
| Permanent | 3.5 ± 0.3 | 1.6 ± 0.5* | 37.5 ± 3.0 | 18.0 ± 3.9* | 71.2 ± 6.8 | 48.4 ± 6.8* | 46.4 ± 7.1 | 28.3 ± 7.1 | 74.6 ± 8.2 | 56.3 ± 11 | 37.0 ± 8.8 | 24.2 ± 8.7 |

*$p < 0.05$

From the data collected, positive treatment with temporary mucosal may be a good indicator of permanent serosal activity and response to GES.

The average impedance recorded for the temporary devices was higher than the permanent devices, 518Ω in contrast to 418Ω ($p=0.7$).

Table 2 lists stimulation parameters along with calculations of charge (in Coulombs), energy (in micro-Joules) and power (in micro-Watts) delivered by GES in this study. There were no known complications from the procedures or the stimulation.

TABLE 2

| | Impedance & Power Values | | | | | |
|---|---|---|---|---|---|---|
| | IMPEDANCE (Ω) | | | TOTAL | | |
| | PEGStim | ENDOStim | Total | Charge | Power | Energy |
| Temporary | 376 | 760 | 518 | 1.7 | 1.2 | 4.3 |
| Permanent | 416 | 437 | 419 | 1.7 | 1.0 | 3.5 |

Standardized Parameters
Amplitude (current)=0.005 A
Frequency=14 HZ
Pulse Width=0.00033 Sec
On time=0.1 SEC
Off time=5 Sec
Formula:
  Duty Cycle (DC)=Frequency×Pulse Width×(On Time/Off Time)
  Charge (micro-Coulomb)=Current×Pulse Width
  Average Power (micro-Watt)=$Current^2$×Impedance×DC
  Energy/Pulse (micro-Joule)=$Current^2$×Impedance×Pulse Width Both Endoscopic and PEG placement of GES electrodes is safe, feasible and rapidly demonstrates effectiveness in treatment of drug refractory gastroparesis. The long-term effects of gastric electrical stimulation are similar to those seen in the temporary phase. Thus, one embodiment of the present invention is the use of tGES stimulation as a predictor of long term outcome of permanent stimulation.

Additionally, the development of specific tools for the placement of tGES electrodes may have application in clinical conditions other than gastroparesis.

Example II

GES for Chemotherapy Induced Refractory Nausea and Vomiting

Summary of Example II

Example II demonstrates that nausea and vomiting of chemotherapy are associated with disturbances of gastric electrical rhythm and that tGES effectively controls the symptoms of nausea and vomiting induced by chemotherapy. Autonomic and enteric changes following stimulation provide a mechanism for effective tGES in patients experiencing chemotherapy induced nausea and vomiting.

Background

Nausea and vomiting are common symptoms at the end of life. These are best studied in cancer patients, and reported in up to 62% of terminally ill patients, with a prevalence of at least 40% during the last 6 weeks of life (1). The mechanism of CIE is thought to be, in part, due to disorders of the autonomic nervous system, and may include an altered enteric nervous system as well.

Six patients receiving Cisplatin for head and neck cancer were studied with electrogastrography (EGG) before, during and after chemotherapy. Changes in gastric electrical activity were seen post-Cisplatin, with an increase in EGG frequency which was temporarily associated with nausea and/or vomiting. Recent work with patients suffering from nausea and vomiting post-surgery for Barrett's carcinoma has shown that tGES effectively controls the symptoms and that this improvement was maintained by permanent GES devices.

The patients with diabetes mellitus (DM) who received GES devices had a statistically significant improved survival over the DM patients who were consented, but not implanted, using a Kaplan-Meier survival curve (6). The symptom improvements seen with tGES correspond to permanent GES.

Example III

Electrostimulation for Intractable Delayed Emptying of Intrathoracic Stomach Following Esophagectomy Summary of Example III The use of the denervated intrathoracic stomach as esophageal substitute can rarely lead to severe delayed gastric emptying. This example describes the use of electrostimulation for this condition. Gastric Electrical Stimulation (GES) is used to treat medically refractory gastroparesis and uses a battery powered neurostimulator connected to the gastric antrum with two electrodes. Electrodes were implanted via a right thoracotomy and tunneled to the right subcostal area where the pacemaker is placed. Two male patients, 52 and 60 years old, who underwent Ivor Lewis esophagectomy for esophageal adenocarcinoma developed medically refractory gastroparesis and were dependent on jejunostomy feeding. Patients initially had endoscopic placement of temporary stimulating electrodes with significant improvement in symptoms and radionucleotide gastric emptying. Patients subsequently underwent implantation of a permanent GES device. Relief of symptoms was persistent with no nausea or vomiting and a decrease of total symptom score from 12.5 and 16 to 5 and 1 (over 20), respectively. Patients with intractable delayed gastric emptying following esophagogastrectomy benefit from a GES device implanted via thoracotomy.

Two male patients, 52 and 60 years old, who had previously undergone an Ivor Lewis esophagogastrectomy for distal esophageal adenocarcinoma, were referred to us for refractory gastroparesis. Both patients developed chronic nausea and vomiting along with anorexia, early satiety, bloating and epigastric pain soon after the surgery. One of the patients who had not had a drainage procedure at the time of the initial surgery underwent a laparotomy for pyloroplasty 2 months after the surgery without relief of his symptoms. Patients did not respond to various prokinetic agents including erythromycin and metoclopramide. They both were dependent on enteral feeding through a jejunostomy to maintain their weight.

At the start of the present GES treatment, total symptom scores were 12.5 and 16 (over 20). Radionucleotide gastric emptying studies showed 25% and 51% gastric retention at 4 hours in both patients, respectively.

Both patients initially had placement of tGES electrodes endoscopically with rapid significant improvement in their nausea score (0 and 0 out of 4), vomiting score (0 and 0 out of 4) and total symptom score (5 and 7 out of 20). Radionucleotide gastric emptying also improved significantly with temporary electrostimulation to 19% and 8% at 4 hours, respectively.

Patients subsequently underwent implantation of a permanent GES device. Postoperative courses were unremarkable. Both patients experienced significant and persistent postoperative relief of symptoms. Nausea and vomiting resolved and the total symptom score improved to 5 and 1, respectively.

Subsequent to esophagectomy and reconstruction with gastric pull-up, the intrathoracic vagally denervated stomach initially thought to act primarily as a passive conduit, now appears to recover more and more motor activity over time, and may even generate complete migrating motor complexes. This motor activity seems to return towards normal in a progression from the pylorus cephalad. Intrathoracic gastric emptying, as evaluated by radioisotope, significantly also increases over time. Even though patients will never eat the way they did before their surgery, most of them will ultimately be able to tolerate smaller more frequent meals and maintain their weight.

Some patients do not improve their gastric emptying and remain significantly symptomatic. Their complaints appear to correlate with the myoelectric and contractile activities of the transposed stomach. They have a higher occurrence of tachygastria on electrogastrography and a decreased postprandial contractile activity on manometry. In these patients with persistent gastroparesis, prokinetic agents should be attempted as the first line of therapy. Both cisapride and erythromycin have been shown to significantly improve gastric emptying of the gastric conduit by stimulating gastric motility. In the rare cases where gastroparesis is refractory prokinetics, patients have no other treatment options and suffer from poor quality of life due to persistent, hard to control symptoms, mainly nausea and postprandial vomiting. They almost exclusively rely on enteral feedings through a jejunostomy in order to provide nutrition.

In the first six patients with refractory post gastric surgery gastroparesis that were implanted with gastric pacemakers, significant improvements were seen in symptoms, health-related quality of life and solid and liquid gastric emptying at long-term follow-up.

Conclusion of Example III

Results from Example III provide evidence that electrostimulation in intractable delayed emptying of the vagally denervated intrathoracic stomach following esophagectomy is an effective treatment. It provides an attractive treatment option for this difficult group of patients, unresponsive to conventional medical therapy and who otherwise have no other alternative. Implanting these pacemakers does require a right thoracotomy, although thoracoscopy may be used, especially following transhiatal esophagectomy. Before embarking in these major operations, the response to electrostimulation must first be assessed by temporary endoscopic pacing which correlates well with response to permanent GES devices. In patients with intractable delayed gastric emptying following Ivor Lewis esophagectomy, symptoms can be significantly improved with electrostimulation. Implantation of the gastric pacemaker in these cases requires a thoracotomy.

Example IV

GES for the Treatment of Colonic Disorders

Example IV is directed to the use of GES in the treatment of colonic disorders, which include constipation, diarrhea and pelvic floor disorders. A comparison was conducted from the results of therapy with GES and sacral electrical stimulation ("SES") in 37 patients implanted with both devices. Patients were 35 females, 2 males, mean age of 44 years-old, with gastroparesis as well as bladder or other pelvic floor dysfunction. 33 patients received their GES before SES. 4 patients had post-surgical gastroparesis, 5 had diabetes mellitus (type I or II), and the rest had idiopathic gastroparesis.

Procedure

Patients were evaluated at baseline, latest, and follow-up (median 4 yrs GES and 2 years SES) using standardized scores of upper GI (UGI: 0-4, UGITSS max 20), lower GI (LGI: 0-3, LGITSS, max 9) and GU (GU: 0-3, UTSS, max 12) function as well as quality of life (QOL) before and after GES and SES. Results were compared by t-tests and reported as mean±SE.

Results of Example IV

In this group of 37 patients, combined gastric and sacral electrical stimulation improved UGI, LGI and GU symptoms including gastric or upper GI total symptom score (UGITSS), bowel or lower GI score (LGISS), and urinary score (UTSS). The quality of life scores improved significantly for each stimulator individually as well as the two stimulators combined. A combined treatment of GES and SES appears to be safe and effective for patients with gastroparesis, bowel problems, and bladder dysfunction.

TABLE 3

| | Upper GI Symptoms | | | | |
| --- | --- | --- | --- | --- | --- |
| | Vomiting | Nausea | Satiety | Abd. Pain | UGITSS |
| Before | 3.4 ± 0.2 | 3.9 ± 0.1 | 3.6 ± 0.1 | 3.7 ± 0.1 | 145 ± 0.4 |
| After | 1.2 ± 0.2 | 2.0 ± 0.2 | 2.0 ± 0.2 | 2.0 ± 0.2 | 7.0 ± 0.7 |
| p-value | <0.001 | <0.001 | <0.001 | <0.001 | <0.001 |

TABLE 4

Lower GI Symptoms

| n = patients | Bowel Incontinence | Urgency | Constipation | Diarrhea/week n = 3 | BM/week* n = 34 | LGITSS |
|---|---|---|---|---|---|---|
| Before | 0.9 ± 0.2 | 1.0 ± 0.2 | 2.2 ± 0.2 | 21.7 ± 15.4 | 0.7 ± 0.2 | 4.0 ± 0.3 |
| After | 0.5 ± 0.1 | 0.6 ± 0.1 | 1.4 ± 0.2 | 4.3 ± 1.6 | 3.0 ± 0.9 | 2.2 ± 0.2 |
| p-value | 0.1 | 0.02 | 0.001 | 0.344 | 0.012 | <0.001 |

*Bowel movements per week for patients with constipation.

TABLE 5

Urinary Symptoms

| | Urinary Incontinence | Urgency | Voiding Diff. | # Pads | UTSS |
|---|---|---|---|---|---|
| Before | 1.3 ± 0.2 | 1.4 ± 0.2 | 2.1 ± 0.2 | 1.4 ± 0.4 | 8.1 ± 0.6 |
| After | 0.5 ± 0.1 | 0.5 ± 0.1 | 0.7 ± 0.2 | 0.3 ± 0.1 | 2.6 ± 0.5 |
| p-value | <0.001 | <0.001 | <0.001 | 0.02 | <0.001 |

TABLE 6

Quality of Life

| | GES | SES | GES and SES |
|---|---|---|---|
| QOL Before | −2.14 ± 0.26 | −1.57 ± 0.28 | −2.29 ± 0.26 |
| QOL After | 1.65 ± 0.32 | 1.89 ± 0.23 | 1.58 ± 0.27 |
| p-value | <0.001 | <0.001 | <0.001 |

Example V

Correlation of Enteric Nervous System and Urologic Parameters in Patients with Symptoms of Gastroparesis This example studies the relationships between these two intra-abdominal organ systems of the foregut and hindgut in GP patients with LU symptoms. 30 patients were studied (6 male and 24 female, mean age of 43 years) with symptoms of GP, 14 of whom had diabetes mellitus and 16 of whom had idiopathic GI disease. All patients underwent the enteric nervous system measure of the electrogastrogram (EGG) as well as urodynamic studies (UD) for co-existent urinary complaints: difficulty in emptying bladder 18/30 (60%), incontinence 15/30 (50%), frequency 13/30 (43%), and/or straining 16/30 (53%).

Procedure

Urodynamic function evaluation was performed via uroflourometry for peak (PK) and mean flow rates in ml/seconds (normal>12 ml/sec) and post void residual volumes (PVR) in ml (normal<150 ml). Multi-channel complex fluid cystometry evaluated bladder capacity (CP) in ml (normal<300) and first sensation (FS) in cc (normal<150). EGG was measured by placing three electrodes over the gastric area as previously reported (GE 98 (2): A 320, 1990) and was reported as average frequency (normal range 2.8-3.3 cpm). Correlations were analyzed by Spearman correlation coefficients between EGG and UD values and predictive values were calculated.

Results of Example V

22/30 (73%) of the EGGs and 28/30 (93%) of urodynamic studies were abnormal. EGG abnormalities correlated significantly with the urodynamic measure of FS (r=0.6, p=0.001). Results of EGG and urodynamic studies are summarized in the Tables 7 and 8 below.

TABLE 7

Number and % Abnormal of EGG and UD by Dx Subgroups

| Measure vs subgroup | Diabetes Mellitus | Idiopathic |
|---|---|---|
| Peak Flow | 6/14 (43%) | 2/14 (14%) |
| Post Void Residual Volume | 4/14 (29%) | 10/16 (63%) |
| Capacity | 12/14 (86%) | 14/16 (88%) |
| First Sensation | 7/14 (50%) | 10/16 (63%) |
| EGG | 11/14 (79%) | 10/16 (69%) |

TABLE 8

Predictive Values for EGG and UD Measures

| | EGG in Dx Subgroups | | | |
|---|---|---|---|---|
| | Diabetes Mellitus | | Idiopathic | |
| UD Measures | Sensitivity | Specificity | Sensitivity | Specificity |
| First Sensation | 86 | 29 | 90 | 83 |
| Capacity | 77 | 100 | 91 | 67 |
| Post Void Residual Volume | 100 | 36 | 60 | 48 |

Conclusion of Example V

Based on this group of patients with symptoms of gastroparesis and lower urinary dysfunction, electrogastrogram abnormalities can predict urodynamic dysfunctions in both diabetic and idiopathic patients.

Example VI

Use of GES for Electrophysiological, Morphological and Serologic Features of Chronic Unexplained Nausea and Vomiting GES was used in patients with unexplained and refractory chronic nausea and vomiting to evaluate and show that GES can be used as an effective treatment in the presence of morphological, physiologic and serologic abnormalities.

Procedure

One hundred and twenty-one consecutive patients were evaluated at the University of Tennessee at Memphis Medical Center, over a ten-year period (1988-1998), for chronic nausea and/or vomiting lasting greater than one year. The evaluation included 16 males and 105 females with a mean age of 37 years (range 13 to 70 years). Symptoms of nausea, vomiting, anorexia/early satiety, bloating/distention and abdominal pain were evaluated on a scale of 0 to 10 (10 being the worst symptoms), and a total gastrointestinal symptom score was obtained from the sum of all five symptoms (scale 0-50).

The primary gastrointestinal diagnoses included diabetes mellitus (7 patients), post-surgical conditions (6 patients), and idiopathic disorders (108 patients). Of those with idiopathic disorders, the majority had detectable abnormalities including collagen-vascular disorder (16), other autoimmune disorders (11), neurological disorders (11), familial disorders (4), dilated bowel (3) and documented infectious cause (1). It was further discovered that on overlap of disorders consisted of migraine, fibromyalgia, interstitial cystitis or endometriosis in 25 patients.

Results of Example VI

79/101 patients had abnormal full-thickness biopsy (70 neuropathies and 9 myopathies), and frequent serum autoimmune abnormalities (mean score 13.2, normal<3.0). 96/101 patients had gastric electrophysiology abnormalities of frequency and/or uncoupling. Patients with small-intestinal myopathy showed a diversity of diagnoses; some patients with neuropathy had abdominal pain that correlated with autoimmune scores on Western Blot.

Data was collected and summarized in Tables 9-11:

TABLE 9

Results of Small Bowel Full Thickness Biopsy (FTB) and Gastric Electro-Physiology (EPS) in all 121 patients

| Test | N | % of total | DM | PS | ID | Normal | Abnormal | Classification of abnormal Myopathy | Neuropathy |
|---|---|---|---|---|---|---|---|---|---|
| Full Thickness Biopsy | 118 | 98% | 7 | 5 | 106 | 26/118 (22%) | 92/118 (78%) | 12/92 (13%) | 12/92 (87%) |
| Serosal EGG | 104 | 86% | 6 | 5 | 93 | 5/104 (4%) | 99/104 (96%) | 9/99 (9%) | 66/99 (66%) |
| Full Thickness Biopsy & Serosal EGG | 101 | 83% | 6 | 4 | 91 | 1/101 (<1%) | 75/101 (75%) | 9/75 (12%) | 66/75 (82%) |

TABLE 10

Propagation in 82 patients with both proximal and distal recordings

| Propagation | Number of patients | Proximal Frequency | Distal Frequency |
|---|---|---|---|
| Neuropathies | 58 | 5.38 ± 0.21 | 5.29 ± 0.23 |
| Myopathies | 7 | 5.87 ± 0.63 | 5.97 ± 0.77 |
| Normal | 17 | 5.40 ± 0.37 | 5.34 ± 0.37 |

TABLE 11

Presence of coupling/uncoupling and of normal/abnormal propagation in 82 patients with both proximal and distal recordings

| Coupling | NORMAL | | | ABNORMAL | | |
|---|---|---|---|---|---|---|
| | N | Proximal Frequency | Distal Frequency | N | Proximal Frequency | Distal Frequency |
| Overall | 37 | 5.78 ± 0.27 | 5.83 ± 0.27 | 45 | 5.17 ± 0.24 | 5.10 ± 0.24 |
| Neuropathies | 26 | 5.72 ± 0.33 | 5.06 ± 0.28 | 32 | 5.16 ± 0.30 | 5.06 ± 0.28 |
| Myopathies | 3 | 7.00 ± 1.20 | 7.00 ± 1.10 | 4 | 5.03 ± 0.61 | 5.20 ± 0.97 |
| Normal | 8 | 5.54 ± 0.52 | 5.52 ± 0.53 | 9 | 5.28 ± 0.53 | 5.18 ± 0.55 |

Conclusion of Example VI

Patients with refractory and unexplained nausea and vomiting have a high incidence of both small bowel morphologic abnormalities (primarily neuropathies) and gastric electrophysiologic abnormalities, which are commonly associated with serologic autoimmune activation. Similar histomorphological, physiologic and serologic measures should be considered in the diagnostic evaluation of any patient with refractory or unexplained nausea and vomiting.

Based on the data collected, GES is effective for treating the aforementioned disorders. Most, if not all, patients with nausea/vomiting have an abnormal EGG/ENS, abnormal ANS and neuropathies, which supports that GES may be helpful for them.

Example VII

Use of GES for the Treatment of Nausea and Vomiting Associated with Pregnancy

Summary

EGG results taken from patients were abnormal, providing evidence that dysfunction of autonomic and enteric nervous systems plays a role in pathophysiological hyperemesis gravidarum. EGG results were different with patients being abnormal (>3.3 cpm): Patients 3.4±0.2 vs. Controls 3.0±0.1, p=0.07). Based on the data collected, Dysfunction of Autonomic and Enteric Nervous Systems play a role in the pathophysiology of Hyperemesis Gravidarum ("HE").

Hyperemesis gravidarum is considered as the severe end of the spectrum of "morning sickness," with no clear separation between the usual nausea and vomiting of pregnancy and hyperemesis gravidarum. Several theories, including psychological, thyroid abnormalities, reproductive hormonal abnormalities, liver abnormalities, disordered gastric electrical activity, abnormal lipids, nutritional causes and autonomic nervous system abnormalities have been proposed. Data from the examples show that HE is related to imbalance in autonomic and/or enteric nervous system functioning.

Procedure 21 post-rehydration HE patients were studied who were hospitalized for ketosis based on laboratory and clinical parameters. In addition, six healthy, pregnant control patients were also studied. There were no statistical differences between patient and control groups in mean age (23 vs. 27 years old), weight (140 vs. 131 lbs.) or gestational age (13.6 vs. 15.1 week). The HE patients were largely multiparous (14 out of 21 patients [66%]) while all but one of the normal controls was multiparous (83%).

Autonomic Function Tests

Two measures of Sympathetic Adrenergic Function (SAF) were performed, each by utilizing capillary photoplethysmography: percent vasoconstriction (% VC) in response to cold stress and Postural Adjustment Ratio (PAR), which is the ratio in response to raising and lowering the arm. One measure of Vagal Cholinergic Function (VCF) was performed: EKG R-to-R interval (RRI); and one measure of sympathetic cholinergic function was performed: resting skin temperature. Total autonomic score (TAS=VC+PAR+RRI) was also calculated, as previously reported. Resting electrogastrography (EGG) in cycles/min was recorded as a noninvasive measure of the enteric nervous system. All patient tests were conducted in the same manner after initial skin temperature and baseline measurements showed stability. No patients showed clinical symptoms of dehydration when studied.

Sympathetic adrenergic tests, % VC and PAR, were assessed. Blood flow was measured via capillary pulse amplitude in the left hand with infrared photoplethysmography, while the right hand was simultaneously inserted into cold water (maintained at 14° C. for 60 seconds). Percent vasoconstriction is a measure of the change in capillary pulse amplitude caused by reflex vasoconstriction and is expressed as percentage of change from baseline. PAR was assessed by measuring blood flow in one hand while that hand was raised, lowered and kept level. PAR was expressed as a ratio of a reflex barostatic response from the baseline. Sympathetic cholinergic function was measured by resting skin temperature in degrees centigrade. PAR and skin temperatures were also measured after ice, used for vasoconstriction.

Vagal cholinergic function was measured as variability in pulse rate during deep respiration, using the R-R interval (RRI) on the EKG with a continuous electrocardiogram strip taken while the patient breathed maximally. The time intervals between RRI's were calculated and a vagal response (expressed as a percentage) was then assessed using the following formula:

$$RRI = ([\text{inspiration time} - \text{expiration time}]/\text{expiration time}) \times 100.$$

Autonomic function data were compared with data from a group of 6 healthy pregnant women and 49 normal volunteers (mean age $19.5 \pm 0.95$ yr.). All three autonomic function test measures were evaluated by sex variable (male or female) in the normal volunteer group, and no significant differences were found between male and female patients in autonomic function test measures.

Resting gastric electrical activity was studied by recording a resting cutaneous tracing for 30 minutes, which was previously correlated well with a 4-hour fasting, and fed EGG. Frequency is reported in cycles/min (normal range is <3.3 cycles/min). These tracings were evaluated visually by three investigators who reviewed tracings in a blinded manner. Values for thyroid and liver function were also compared for normal controls.

Statistical Analyses

AFT and EGG results were compared by t-tests between HE patients and controls, and by Spearman correlation coefficients within the HE and the control groups, and within the normal and the abnormal EGG subgroups to compare autonomic measures of patients with those of controls. All t-tests were two-tailed and statistical significance for t-tests were designated at the 0.05 level using a Bonferroni correction factor for multiple comparisons. All data analyses were conducted via the CLINFO software package (Bolt, Beranek, and Newman, Boston, Mass.) in conjunction with Statistical Analyses Systems (SAS Institute, Research Triangle, N.C.) on a VAX 11/750 mainframe located at the clinical research center, or by PC!Info, a DOS version of CLINFO.

Results of Example VII

Measures of autonomic functions (VC, PAR, RRI) were obtained in all 21 patients and 6 controls. The sympathetic adrenergic measure of percent vasoconstriction (% VC) did not show a statistical difference in the HE group compared to pregnant controls (mean $79.4 \pm 4.15$ vs. $87.23 \pm 3.56$, $p=0.17$). The sympathetic adrenergic measure PAR, however, was significantly lower in HE patients than in the control group (mean $24.47 \pm 5.04$ vs. $67.63 \pm 11.41$, $p<0.01$). Significant differences were also found in Sympathetic Adrenergic Function Index (SAFI=VC+PAR: HE group mean $103.4 \pm 9.4$ vs. control group mean $154.9 \pm 14.3$, $p<0.05$, normal). Likewise, the vagal cholinergic measure of R-R interval was significantly lower in the HE group than in the controls (mean $29.98 \pm 2.95$ vs. $40.91 \pm 2.38$, $p<0.05$). Skin temperature, a sympathetic cholinergic measure, was lower in patients, as compared to controls (mean $31.2 \pm 0.6$ vs. $33.8 \pm 0.5$, $p<0.01$). The global measure of Total Autonomic Score (TAS, the sum of VC+PAR+RRI) was also lower in HE patients (HE group mean $131.75 \pm 9.61$ vs. control group mean $196.87 \pm 12.8$, $p<0.05$).

EGG results revealed that the control group had a normal EGG frequency at $3.04 \pm 0.05$ cycles with a range of 2.9 to 3.2 cycles per minute, while HE patients had a mean of $3.35 \pm 0.16$ cycles per minute: higher than the normal range, but of borderline significance from controls ($p=0.07$). A subgroup of 7 HE patients with EGG's in the abnormal range (>3.3 cycles per minute), however, showed a correlation between higher EGG frequency and the sympathetic adrenergic measure PAR after ice ($r=-0.64$, $p<0.010$). Thyroid functions (T3 and T3RU) were found to be decreased in patients who had abnormal VC ($r=0.5$, $p<0.03$) and R to R interval ($r=0.5$, $p=0.02$), respectively. Also, liver transaminases vs. SGOT and SGPT were decreased in those with an abnormal PAR ($r=-0.5$, $p=0.01$) and R to R interval ($r=0.7$, $p<0.001$).

Discussion of Example VII

Using standardized and well-characterized non-invasive methods, a well-defined group of patients were assessed who met the criteria for hyperemesis gravidarum. Patients found with hyperemesis have blunted autonomic nervous system measures when compared with healthy pregnant controls. Similar blunting of response has been reported previously in-patients with diabetes mellitus. These findings provide evidence that suggest the presence of altered autonomic neuro-systemic function is associated with the patients' symptomatic nausea and vomiting. The same patients who had abnormalities in their thyroid and liver functions also had abnormalities in their autonomic function test results.

Abnormalities were found in the enteric nervous system measure of the electrogastrogram or EGG between HE patients and pregnant controls. EGG abnormalities have been previously reported in nausea and vomiting of pregnancy and HE. However, these EGG abnormalities have never been compared with the results of simultaneous system autonomic function testing in HE. In a subgroup of HE patients with abnormal EGG recordings, the EGG values correlated with the sympathetic adrenergic measure of PAR after ice, indicating that the enteric nervous system abnormalities of some HE patients may relate closely to autonomic dysfunction.

Several aspects of AFT methodology need to be mentioned. First, the patient's level of hydration can affect autonomic testing results. However, in this study, all HE patients were clinically rehydrated. While AFT measures have traditionally been related to the study of cardiovascular autonomic responses, here they were applied to gastrointestinal function.

However, a number of studies have shown that general autonomic responses may reflect gastrointestinal function. While this data may be primarily descriptive, these findings provide new evidence to the mechanism of HE. In addition, the data in this report provides evidence that HE is related to imbalance in the autonomic and/or enteric nervous systems. If this imbalance does play a role in pathophysiology, then drug, device or behavioral therapies for HE that address these abnormalities should be useful in the care of HE.

Conclusion of Example VII

HE is a poorly understood disorder with little certainty about its pathogenesis. Although many theories have been proposed to explicate this syndrome, including thyroid or liver dysfunction and psychological or behavioral abnormalities, none has been defined as the primary cause. In this example, there was significant blunting of autonomic and enteric responses in HE patients, as compared to pregnant controls. Based on the data collected, the autonomic and enteric nervous systems plays a role in modulating primary symptoms in HE, and GES can provide an effective treatment.

Example VIII

GES for Drug Refractory Gastroparesis

Drug refractory gastroparesis has previously been without acceptable alternative therapies. Although Gastric Electrical Stimulation (GES) has been used for over a decade, no long-term multi-center data exists.

Procedure 214 consecutive drug refractory patients with the symptoms of gastroparesis were studied (146 Idiopathic, 45 Diabetic, 23 Post-Surgical), and consented in a variety of clinical research and clinical protocols at three centers from January 1992 through January 2005, resulting in 156 patients implanted, with the other patients serving as controls. Patients were stratified into 3 groups: 1) consented but never permanently implanted; 2) implanted with permanent device; and 3) consented while awaiting a permanent device and followed over time for gastrointestinal symptoms; solid gastric emptying; health related quality of life; and survival, device retention and complications. Demographics, descriptive statistics and t-tests were compared between baseline and latest follow-up.

The implanted stimulation system included a neurostimulator device (Medtronic ITREL 3 Model 7425G or Enterra) and two intramuscular leads (Medtronic Model 4351 or 4300). The leads were inserted into the muscularis propria of the stomach by laparoscopy or laparotomy. They were implanted 1 cm apart along the greater curvature of the stomach 10 cm from the pylorus, and then connected to the neurostimulator device, which was placed subcutaneously in the abdominal wall. Using a programmer (Medtronic Model 7432 Physician Programmer and Model 7457 Memory Mod Software), the neurostimulator was programmed to standardized parameters (frequency, 14 Hz; amplitude, 5 mA; pulse width 330 microsecond μs; cycle ON, 0.1 sec; cycle OFF 5.0 sec). Some patients (approximately 10%) underwent an algorithmic adjustment of stimulation parameters to optimize symptom response.

The patients were evaluated at baseline and at 3, 6 and 12 months, and yearly thereafter, to monitor the vomiting frequency score (VFS), total gastrointestinal symptoms score (TSS), health-related quality of life (HRQOL) and gastric emptying data reported for this paper are: baseline and most recent follow-up evaluation.

The VFS was assessed by the patients' daily record of vomiting episodes over the week preceding their evaluation (Score 0—no vomiting; 1—one or two episodes/week; 2—three or four episodes/week; 3—five or six episodes/week; 4—seven or more episodes/week). The TSS was assessed by the frequency and severity of gastrointestinal symptoms (nausea, vomiting, early satiety, distension/bloating and epigastric pain) on a scale of 0 to 4 (Score 0—absent; 1—mild; 2—moderate; 3—severe; 4—extremely severe; with a maximum possible score of 20). Solid-phase gastric emptying was documented by using a standardized scintigraphic method and a low-fat test meal, or its predecessor, as previously reported. Gastric retention at 1, 2 and 4 hours after ingestion of the test meal was recorded and compared with previously standardized norms. Delayed emptying for clinical use was at 4 hours>10%.

HRQOL was assessed at baseline and at scheduled follow up visits evaluated by an Investigator Derived Independent Outcome System (IDIOMS), a health resource tool incorporating measures of severity of illness (SOI), intensity of services delivered (ISO) and organ systems involved (OSI). Each of these was scored by a physician familiar with the patients, and were rated 0-10, none to greatest, for each point in time (baseline and latest follow-up), maximum score 30. IDIOMS has been demonstrated to correlate with both GI symptoms and health related costs in patients with the symptoms of gastroparesis undergoing drug, device or behavioral treatments. IDIOMS correlates highly with standard HRQOL measures, such as the Sickness Impact Profile or SIP. In a prior unpublished study, it was found that spearman correlation coefficients range from r=1.0 between the SIP Physical Dimension Profile and IDIOMS, to r=0.88 with the Psychological General Well-Being scale, a predecessor of the SF-36. IDIOMS captures generically the functional aspects of illness, as well as a measure of intensity of healthcare resource utilization. The health resource measure, IDIOMS, one of several HRQOL instruments used in a number of the individual trials, was the only common measurement tool for all patients, and thus is the measure reported here.

Patients were followed for the following outcomes over time, using the last available data for each patient as the final outcome point: gastrointestinal symptoms; gastric emptying; health related quality of life; and survival, device retention, and complications. Additional sub-analysis was performed to analyze response to GES therapy by Vomiting, Nausea, Total Symptoms Score. Kaplan-Meier survival curves were constructed for all patients consented and compared by subgroups of implanted vs. non-implanted and diabetic vs. non-diabetic subgroups, analyzed by log-rank Chi-square analysis and reported as % survival with 95% confidence intervals (CI). Data from baseline evaluation and the latest follow up was analyzed, and demographics, descriptive statistics and paired t-tests were compared between baseline and latest follow-up and reported as mean±SE.

At latest follow-up, median 4 years for 5,568 patient months, most patients implanted (135 of 156) were alive with intact devices, significantly reduced GI symptoms, improved health related quality of life, with evidence of improved gastric emptying, and 90% of patients had response in at least 1 of 3 main symptoms. Most patients explanted, usually for pocket infections, were later re-implanted successfully. There were no deaths directly related to the device.

Results of Example VIII

Consecutive Consenting Patients: 214 consecutive individual patients, consenting to a variety of clinical research and research protocols: 45 male, 169 female, mean age at consenting 42 years, followed for a median 4 years for 4447.7 patient months or 370.7 patient years. Patients had the following initial diagnoses of drug-refractory gastroparesis: 146 Idiopathic (ID), 42 Diabetic (DM), and 26 Post-Surgical (PS). At latest follow-up: 25 patients were consented but never implanted, 49 patients had temporary followed by permanent implant, 107 patients had permanent devices alone and 33 patients had temporary devices awaiting permanent devices.

Of the 214 patients consented in 1992-2005, 20 patients were enrolled in more than one study, due to protocol eligibility reasons. Patients in group 1 (consented for >1 year but never permanently implanted) did not receive implants due to insurance approval/reimbursement issues. There was no statistical difference in any of the parameters (VFS, TSS, HRQOL or GET) between groups 1 and 2 at baseline. At follow up, patients were stratified by number of consenting patients by group at inclusion:

- 25 patients in groups 1 (consented only): 17 ID, 6 DM and 2 PS.
- 156 patients with permanent implants in group 2 (implanted): 49 implanted with a temporary followed by permanent device, and 107 implanted with a permanent device alone; underlying diagnosis: 107 ID, 32 DM and 17 PS.
- 33 patients in group 3 (temporary only): 22 ID, 7 DM and 4 PS.

Long Term Data on Patients Implanted: A significant reduction in symptoms was observed in patients with permanent device implants at latest follow up compared to baseline. VFS (range 0-4) was reduced from 2.9±0.1 to 1.9±0.2 ($p<0.001$). GI total symptom score (range 0-20) improved from 15.6±0.3 to 10.9±0.2, $p<0.001$). HRQOL by IDIOMS (scale 0-30) improved significantly from 16.3 to 10.6, ($p<0.005$).

Of the patients with long term follow-up analysis by 3 main symptoms (baseline vs. latest) revealed: Vomiting: 62% Improved, 37% not improved; Nausea: 59% improved, 41% not improved; Total Symptom Score: 84% improved, 16% not improved. If all non-vomiters were excluded, vomiting was 70% improved and 30% not improved. 90% of patients had a response in at least 1 of 3 parameters.

A significant acceleration in gastric emptying was noted at latest follow up compared to baseline: The 2 hour gastric retention decreased from 55% to 42% ($p<0.001$). The 4 hour gastric retention improved from (26% to 17) ($p<0.001$).

A total of 24 of 214 patients (11.3%) consenting patients died. Life table analysis results revealed no significant difference between all patients implanted: 30 mo survival 90% (CI 84.6-95.4%) and 36 mo 85.6% (CI 78.5-92.7) vs. all non-implanted patients: 30 and 36 mo survival 79.5% (CI 62.9-98.9 for both). All diabetic paitents had lower survival: 30 mo survival 85% (CI 73.1-97.3) and 36 mo 58.6% (CI 37.5-79.7) vs. all non-diabetic patients: 30 mo survival 91.1% (CI 86.0-96.2) and 36 mo 85.2% (CI 77.8-92.6) ($p<0.01$ by log-rank Chi-Square test). Non-implanted diabetic patients had higher mortality/lower survival: 30 and 36 mo survival 33.3% (CI 0-80.0 for both) vs. diabetic implanted patients: 30 mo survival 95.4% (CI 86.7-100) and 36 mo 60.7% (CI 33.0-88.4) ($p<0.05$ by log-rank Chi-square test). Cause of death was primarily due to underlying disease and was not determined to be directly related to the GES device in any patient. 11 of 123 patients (8.9%) had devices explanted (64% due to infection and 36% for technical reasons). Most (10/11) patients have since been successfully re-implanted.

Discussion of Example VIII

Example VIII demonstrates that gastric electrical stimulation using a low energy stimulus administered at a frequency that is higher than the normal slow wave frequency improves symptoms and gastric emptying in patients with drug refractory gastroparesis. The technique of gastric electrical stimulation applied to these patients, often labeled high-frequency/low-energy stimulation is distinctly different from low-frequency, high energy electrical therapies, often referred to as gastric pacing. Unlike gastric pacing, gastric electrical stimulation is available as an implantable device, suited for long-term trials of therapy, and is the only FDA approved electrical therapy for drug-refractory gastroparesis. The data shows that the improvement in gastroparesis symptoms with GES is sustained over time, and that long-term gastric electrical stimulation is safe.

Several short-term studies have previously examined the effects of electrical stimulation on symptoms and gastric motility. In the GEMS study 18 patients with a permanent gastric electrical stimulator implant, had follow up for a mean period of 30 months. There was a significant improvement in nausea, vomiting, patient and physician rated quality of life. In the WAVESS study 33 patients with chronic gastroparesis (17 diabetic and 16 idiopathic) received continuous high-frequency/low-energy gastric electrical stimulation. Scores for symptom severity and quality of life significantly improved ($p<0.05$) at 6 and 12 months, and gastric emptying was modestly accelerated. In the present study, improvement in scores for symptom severity and quality of life was sustained for a median duration of 36.7 months (range 1 to 105 months). Date provides evidence that gastric electrical stimulation might favorably affect gastric emptying when applied over a longer period and in this report, solid gastric emptying improved significantly over time.

It has been previously reported that a practitioner-rated diagnostic and predictive score (similar to IDIOMS here) correlates with quality of life improvement in gastroparesis patients undergoing gastric electrical stimulation (reported in Cutts T F, Luo J, Starkebaum W, Rashed H, Abell, T L, "Is gastric electrical stimulation superior to standard pharmacologic therapy in improving GI symptoms, healthcare resources, and long-term health care costs?," Neurogastroenterol Motil, 2005; 17: 35-43; herein incorporated by reference) consistent with previous reports with pharmacotherapy (reported in Cutts T F, Abell T L, Karas J G, Kuns J., "Symptom Improvement from prokinetic therapy corresponds to improved quality of life in patients with severe dyspepsia," Dig Dis Sci 1996; 41:1369-1378; herein incorporated by reference). The data of Example VIII provides evidence that an improvement in HRQOL by the health resource measure IDIOMS, which reflects illness severity, health services provided and organ system involvement in a large multi-center sample of patients over time.

Example VIII also establishes the durability of the present GES device. Of the 123 patients with permanent devices, 11 patients have undergone explant: 7 for infections and 4 for technical reasons and 10/11 have been reimplanted.

This multi-center report is the first to compare long-term survival of patients undergoing GES for drug refractory gastroparesis with historical controls. 19 of 123 patients have died, most from their primary illnesses. Patient deaths were higher for diabetic patients than non-diabetic patients consented. Patient deaths were lower for diabetic patients with GES than diabetic non-implanted controls. However, the number of diabetic non-implanted controls was small, and hence a survival benefit cannot be proven based on this cohort alone. There have been no deaths directly attributable to the devices.

The data from Example VIII shows that the effect of gastric electrical stimulation can be sustained for a median of 48 months in a substantial proportion of severe gastroparesis patients with previously intractable symptoms. The data also clearly shows that gastric electrical stimulation favorably affects gastric emptying when applied over a long period of time. Continued efforts to identify which patients will benefit most, and under what conditions, are warranted. In conclusion, gastric electrical stimulation has shown itself to be both safe and effective over the last decade during clinical use in three centers from one region.

Example IX

GES Use in Endoscopic Maneuvers of the Stomach Demonstrating Physiologic Characteristics of the Electrogastrogram (EGG)

This example demonstrates the correlation of EGG with the use of GES.

Procedure 10 female GP patients (mean age 43 years, GP etiology: 1 diabetic, 9 idiopathic) underwent permanent gastric electrical stimulation (GES) system implantation. Intraoperatively, after seromuscular electrode placement but prior to abdominal closure, EGG recordings were performed sequentially for at least five minutes during the following periods: stomach partial inflation during endoscopy (baseline=Base), endoscopic maximal insufflation (R1), desufflation (D1), re-insufflation (R2), and repeat desufflation (D2). EGG recordings were analyzed qualitatively for rhythm (regular=Reg vs. irregular=Irreg) and amplitude (Equal or UnEqual) and quantitatively for mean frequency (Freq, in CPM) and amplitude (Amp, in mV) as well as the Freq/Amp ratio (FAR). Results were compared for differences from baseline frequency (base to R1) and between R1 and R2 by paired t-tests.

Results of Example IX

After the initial Base period, the R2D2 maneuvers demonstrated more regularity and equal amplitude in the desufflation periods (D1 and D2). There was an initial decrease then stabilization in frequency (p=0.002 for R1 from baseline and p=0.04 between R1 and R2). In the insufflation and desufflation periods, a progressive decrease in amplitude was noted (p<0.02 for R2 and D2 from baseline) and a gradual increase in the FAR were noted (p>0.05). (See Table 12 below).

TABLE 12

| Session | Freq | Reg | Irreg | Amp | Equal | UnEqual | FAR |
|---|---|---|---|---|---|---|---|
| Base | 6.3 | 2 | 8 | 0.84 | 8 | 2 | 17.5 |
| R1 | 4.6* | 4 | 6 | 0.46 | 8 | 2 | 24.9 |
| D1 | 5.9 | 8 | 2 | 0.39 | 10 | 0 | 25.9 |
| R2 | 5.7# | 3 | 7 | 0.37* | 7 | 3 | 26.0 |
| D2 | 6.1 | 8 | 2 | 0.32* | 9 | 1 | 28.1 |
| p value from base | *0.002 | | | *<0.02 | | | NS |
| p value change R1 to R2 | #0.04 | | | NS | | | NS |

Conclusion of Example IX

Intraoperative serosal EGG recordings, when provoked by physiologic maneuvers, show reproducible characteristics in gastric electrical activity. EGG recordings of the relaxed stomach consistently display a more regular rhythm and equal amplitude than with the distended stomach. Maintenance of FAR both when relaxed and distended may be a measure of gastric homeostasis. Standardization of the EGG in terms of gastric distention may be needed for accurate physiologic interpretation.

Example X

GES Study Demonstrating the Importance of Baseline Physiologic Measures tGES improves nearly all parameters studied but the ON/OFF group did better than the OFF/ON group (NGM 19 (6) A15, 2007). It is believed that this result was due to a residual carryover ON effect. To evaluate this, Example X examined a subset of 34 consecutive patients (from the original 58) to see if the randomized group effects persisted long term.

Procedure 58 patients (11 males, 47 females, mean age 46 years) were studied with the symptoms of gastroparesis (GP) and underlying diagnosis: (Idiopathic (ID), n=38; Diabetes Mellitus (DM), n=13; Post-surgical (PS), n=7) in a randomized placebo-controlled study of TGES. The tGES was switched from ON to OFF in one group and OFF to ON in a second group during two consecutive four day sessions. Next, a subset of 34 patients (from the original 58) were studied who later underwent permanent GES, with a mean follow-up of 22.4 months, to see if the randomized group effect persisted long term. All baseline characteristics were examined, including symptoms and physiologic measures and vomiting outcome score, and compared the ON/OFF group (Session 1=ON, Session 2=OFF) to the OFF/ON group (Session 1=OFF, Session 2=ON). Means and standard deviations were compiled by patient group: OFF/ON and ON/OFF.

Results of Example X

Significant group differences were found for 3 outcomes following permanent stimulation: vomiting, mean±SD=0.72±1.29 in the ON/OFF group vs. 1.98±1.53 in the OFF/ON group (p=0.01), Total Symptom Score=8.66±5.87 in the ON/OFF group vs. 13.30±5.00 in the OFF/ON group (p=0.01) and endoscopic mucosal EGG Frequency/Amplitude (F/A) Ratio=6.59±4.86 in the ON/OFF group vs. 19.65±27.41 in the OFF/ON group (p=0.02). (See Table 13 below).

TABLE 13

Permanent Data by Double Masked OFF & ON Groups

| Measure | ON/OFF Group | OFF/ON Group | P-value |
|---|---|---|---|
| Vperm | 0.72 ± 1.29 | 1.98 ± 1.53 | P = 0.01 |
| TSSperm | 8.66 ± 5.87 | 13.30 ± 5.00 | P = 0.01 |
| F/A Ratio | 6.59 ± 4.86 | 19.65 ± 27.41 | P = 0.02 |

Conclusion of Example X

Although a definitive randomization plan was used to assign patients to groups, the differences in long-term outcomes may be due in part to group differences in physiologic characteristics at baseline. Thus, the importance of the baseline mEGG and, especially, the FAR or fT is shown.

Example XI

Correlation of Mucosal and Serosal EGG Probes with Gastric Emptying and Gastric Neuro-Muscular Status The EGG data are reported as average frequency (freq) in cycles per minute, average amplitude (amp) in millivolts, and as the frequency/amplitude ratio (FAR).

Results of Example XI

As shown in Table 14, mucosal amplitude correlated with the outer muscle CD117 cells and mucosal amplitude, frequency, and FAR correlated with the 4-hour GET (p=0.05 to 0.10 by correlation coefficients).

TABLE 14

Serosal and Mucosal EGG Correlations with ICC in Inner and Outer Muscle Layers

|  | Outer muscle correlation and p value | Inner Muscle correlation and p value | GET 4 hour correlation and p value |
|---|---|---|---|
| Serosal amplitude | −0.17/0.43 | −0.07/0.74 | −0.01/0.97 |
| Serosal frequency | 0.05/0.80 | −0.01/0.97 | 0.08/0.71 |
| Serosal FAR | −0.04/0.85 | 0.02/0.91 | 0.05/0.78 |
| Mucosal amplitude | 0.32/0.10 | 0.13/0.53 | −0.33/0.09 |
| Mucosal frequency | −0.19/0.35 | −0.05/0.80 | 0.39/0.05 |
| Mucosal FAR | −0.06/0.75 | −0.05/0.82 | −0.35/0.07 |

Example XII

Predictors of Improvement after Electrical Stimulation in Gastroparesis

Summary 394 consecutive GP patients (320 F, 74 M, mean age 43 years) were consented for GES over 15 years, with diagnoses: 240 idiopathic (ID), 103 diabetes mellitus (D) and 51 post-surgical (PS). To predict response to pGES 150 patients underwent tGES prior to pGES (ID 88, D 40, PS 22). All patients were assessed by symptom scores [nausea (N), vomiting (V), and total symptom (TSS) and IDIOMS (a HRQOL measure) at baseline (b), after tGES (t) and at the latest (L) follow-up after GES, as well as a ratio (Rt) of frequency to amplitude in tGES mucosal EGG. Linear regression determined independent variables predicting the latest vomiting score. Data collected from Example XII is provided in Table 15 below.

TABLE 15

Subset Analysis

| Independent Variable | All t(p) | Idiopathic t(p) | Diabetic t(p) | Post-surgical t(p) |
|---|---|---|---|---|
| Age | −2.49 (0.001) | −1.86 (0.06) | −1.2 (0.23) | 0.28 (0.78) |
| Vb | 3.5 (<0.001) | 3.23 (0.001) | 1.79 (0.08) | 1.04 (0.31) |
| Rt | 2.61 (<0.01) | 2.35 (0.02) | −0.56 (0.57) | 1.060.3) |

Based on the data, the independent predictors of response (age, Vb score and Rt) were most significant in ID patients. Endoscopic tGES mucosal EGG derived Rt is an accurate predictive criterion of symptom improvement with GES, especially improvement in vomiting.

Example XIII

Refractory Gastroparesis Following Roux-en-Y Gastric Bypass

Introduction

Nausea and vomiting are the most common complaints following Roux-en-Y gastric bypass. When these symptoms persists, patients should be investigated in order to rule out a variety of possible etiologies, including anatomic problems such as anastomotic stricture and small bowel obstruction or behavioral problems such as disordered eating. Gastroparesis is a motility disorder of the stomach, defined by delayed gastric emptying of a solid meal in the absence of mechanical obstruction. It can occasionally be responsible for severe, persisting nausea and vomiting symptoms in some of these patients and is a diagnosis of exclusion. It can be difficult to treat and is often refractory to medical therapy. Gastric Electrical Stimulation (GES) has received FDA Humanitarian Use Device approval in 2000 and has been shown to be an effective treatment alternative in patients with medically refractory diabetic or idiopathic gastroparesis. Example XIII evaluates the role of electric stimulation therapy in patients with severe gastroparesis complicating Roux-en-Y gastric bypass for morbid obesity.

Procedure

All patients with refractory gastroparesis following Roux-en-Y gastric bypass surgery for morbid obesity were identified. Chart review was conducted including records from the referring institution. Symptoms of nausea, vomiting, bloating/distension, early satiety and abdominal pain are assessed at all stages of treatment and follow-up and are each scored on a scale from 1 to 4 based on severity, 4 being most severe. The sum of all 5 symptom scores constitutes the total symptom score (TSS), 20 being the highest and worst score possible.

Behavioral problems are ruled out by careful assessment by nutritionists and psychologists. Anatomic problems are ruled out using numerous diagnostic studies including upper gastrointestinal contrast studies, CT Scan of the abdomen and pelvis and upper endoscopy. Diagnosis of gastroparesis is confirmed by radionucleotide gastric emptying showing either significant gastric retention at 4 hours or rapid emptying of the stomach at 1 hour. This test is repeated following the institution of GES therapy.

GES in the example, uses low energy stimuli administered at a frequency higher than the intrinsic slow-wave frequency of the normal stomach. Temporary endoscopically-placed stimulation is used first to assess response to stimulation prior to surgically implanting a permanent device. Permanent GES is implanted surgically via laparotomy. Two stimulating electrodes (Medtronic Model 4351 or 4300) are inserted into the muscularis propria 1 cm apart in the gastric pouch or in the gastric antrum, 10 cm proximal to the pylorus, in cases of reversal of the gastric bypass. When a total gastrectomy with esophagojejunostomy was performed, electrodes are inserted in the proximal Roux limb. Intraoperative endoscopy is used in all cases to verify that the electrodes placed in the stomach or small bowel wall have not penetrated the mucosa. The electrodes are tunneled through the fascia and connected to a battery powered neurostimulator (Medtronic ITREL 3 Model 7425G or Enterra) placed in a subcutaneous pocket. The neurostimulator is programmed and turned on after verifying adequate impedance.

Results of Example XIII

Six patients were referred to our institution for refractory gastroparesis following prior Roux-en-Y gastric bypass. Two patients had a concomitant hiatal hernia repair and truncal vagotomy at the time of their bariatric surgery. All six patients were women with mean age of 42 years. Mean total symptom score at presentation was 15. The onset of symptoms varied among the patients, from immediately postoperatively to 16 years following the surgery.

In addition to the many diagnostic studies to rule out anatomic problems, most patients had a surgical re-exploration that was normal. All patients did not respond to various prokinetic and antiemetic agents. Two patients ultimately had reversal of their surgery with gastrogastrostomy while another had a total gastrectomy with persistence of the symptoms in all three of them.

All patients had markedly abnormal radionucleotide gastric emptying with 4/6 patients showing slow gastric emptying with mean gastric retention of 78% at 4 hours and 2/6 patients with rapid gastric emptying with mean gastric retention of 27% at 1 hour. Temporary endoscopic pacing was performed on all patients with improvement in their total symptom scores to a mean of 8; in addition, gastric emptying improved to 35% at 4 hour in the delayed group and to 30% at 1 hour in the rapid group.

Five of the patients evaluated had insertion of a permanent gastric pacemaker, with implantation of the pacing leads on the gastric pouch (2 patients), the antrum of the reconstructed stomach (1) or proximal Roux limb (2 patients). Symptoms improved significantly postoperatively with mean nausea score of 1.5/4, mean emesis score of 2.2/4 and mean total symptom score of 10.5/20. There was also a persistent improvement in gastric emptying postoperatively based on radionucleotide testing; the delayed emptying group improved to 28% at 4 hour and the rapid emptying group improved to 57% at 1 hour.

Example XIV

GES Improves Symptoms of Post-Surgical Disordered Gastric Emptying

Patients with post-surgical DGE who underwent permanent GES implantation had significant improvement in DGE symptoms on long-term postoperative follow-up. Furthermore, 6 of the 11 patients whom were previously Delayed, and 3 of the 5 patients whom were previously Rapid, exhibited sustained improved gastric emptying (toward normal) after permGES placement. Data from the example are presented in Table 16, below.

TABLE 16

DGE Symptoms before and after permGES

| | Nausea | Vomiting | Total Symptom Score |
|---|---|---|---|
| Baseline | 3.29 ± 0.20 | 2.73 ± 0.21 | 14.2 ± 065 |
| After permGES | 1.96 ± 0.30 | 0.89 ± 0.21 | 8.4 ± 0.85 |
| Change from baseline | 40.4% | 67.4% | 40.8% |

*p < 0.05

In patients suffering from symptomatic refractory post-surgical disordered gastric emptying, permanent placement of gastric electrical stimulation system should be considered a viable option for symptom control.

Example XV

GES Use in Rapid Gastric Emptying

To evaluate tGES therapy, 38 patients with symptoms of gastroparesis (GP) stratified by rapid, normal, or delayed GET.

Procedure 38 patients with GP symptoms were treated with tGES (Am J of Gastro 98: S226, 2003). Patients were stratified by scintigraphy GET (Am J Gastro 95: 1456-1462, 2000): Delayed, 4 hr GET>10%; Rapid: 1 hr GET<37%, and Normal, 4 hr GET<10% & 1 hr GET>37%. Before and after GES, gastric retention and AUC were summed to obtain total gastric emptying (Tge) and total AUC (Tauc). GET data and total symptom score (TSS: sum of vomiting, nausea, early satiety, bloating, fullness & epigastric pain) analyzed by t-test & reported as mean±SE.

Results of Example XV

Delayed patients showed significant improvement in TSS and all GET parameters after tGES. Rapid patients showed significant improvement in TSS and GET as assessed by Tge.

Conclusion of Example XV

The 10th percentile of 1 hour gastric retention of 37% or less is a useful parameter for identifying patients with rapid gastric emptying. Total gastric emptying or total area under the curve may be useful parameters for assessing global improvement in GET. tGES is effective in treating severe symptoms in patients with gastric dysmotility disorders such as those with delayed or rapid emptying. Data from the example is in Table 17, below.

TABLE 17

| | Delayed (n = 24) | Normal (n = 7) | Rapid (n = 7) |
|---|---|---|---|
| GET: 1 hr (before/after) | 79.1 ± 2.6/71.2 ± 3.4* | 61.1 ± 3.0/64.6 ± 6.7 | 21.3 ± 4.6/45.9 ± 10.90** |
| GET: 2 hr (before/after) | 63.2 ± 3.3/49.9 ± 3.9* | 30.1 ± 4.8/39.6 ± 5.9 | 5.4 ± 2.3/18.1 ± 4.9** |
| GET: 4 hr (before/after) | 33.5 ± 3.7/24.0 ± 4.3* | 4.6 ± 1.1/22.0 ± 7.3** | 2.0 ± 1.1/3.7 ± 1.9 |
| Tge (before/after) | 176 ± 8.6/145 ± 10.8* | 96 ± 6.4/126 ± 17.3 | 28.8 ± 6.6/67.7 ± 15.8* |
| Tauc (before/after) | 0.64 ± .03/0.55 ± .03* | 0.40 ± .02/0.49 ± .05 | 0.2 ± .02/0.32 ± .04** |
| TSS (before/After) | 13.9 ± .96/3.1 ± .76* | 13.7 ± 2.7/6.3 ± 2.8** | 15.9 ± 1.3/6.7 ± 3.8* |

*p < .05 before v. after;
**p > .05 < .10

Example XVI

GES Refractory Gastroparesis Following Roux-en-Y Gastric Bypass

GES is used in patients having a rare complication of Roux-en-Y gastric bypass in which gastroparesis is a rare complication. Typical symptoms include nausea and vomiting. In this study, six patients, all women with mean age of 42 years, were identified. Two patients ultimately had reversal of their surgery with gastrogastrostomy while another had a total gastrectomy with persistence of symptoms in all three. Five of the patients evaluated had insertion of a permanent gastric pacemaker, with pacing lead implanted on the gastric pouch, the antrum of the reconstructed stomach or the proximal Roux limb. Nausea and emesis improved significantly postoperatively; mean total symptom score decreased from 15 to 11/20. There was also a persistent improvement in gastric emptying postoperatively based on radionuclide testing.

Based on the results, electrical stimulation is a viable option in selected patients with gastroparesis symptoms complicating gastric bypass and should be considered in lieu of reversal surgery or gastrectomy.

Example XVII

Predictors of Improvements after Electrical Stimulation in Gastroparesis

This example examines long-term outcomes in a large group of GP patients to define clinical and tGES-derived mucosal electrogastrogram criteria that may predict outcome to pGES.

Procedure 394 consecutive GP patients (320 female, 74 male, mean age 43 years) were consented for GES over 15 years, with diagnoses: 240 idiopathic (ID), 103 diabetes mellitus (D) and 51 post-surgical (PS). To predict response to pGES 150 patients underwent tGES prior to pGES (ID 88, D 40, PS 22). All patients were assessed by symptom scores [nausea (N), vomiting (V), and total symptom (TSS)] and IDIOMS (a health-related quality of life measure) at baseline (b), after tGES (t) and at the latest (L) follow-up after GES, as well as a ratio (Rt) of frequency to amplitude in tGES mucosal EGG. Linear regression determined independent variables predicting the latest vomiting score.

Results of Example XVII

Median follow-up was 57 months (range 10 months to 12 years). In analysis by etiology, virtually all patients (I, $p<0.001$, DM, $p \leq 001$ and PS, $p \leq 0.001$) had very good responses. Among all GP patients linear regression analysis identified 3 predictors of improvement in vomiting scores: patient age, baseline vomiting score and Rt. In subset analysis, these predictors were most significant for ID. Among all categories of GP, linear regression analysis identified a low Rt derived by the use of mEGG as the single best predictor of response to tGES and pGES.

The following data was collected and summarized in Table 18.

TABLE 18

Subset Analysis

| Independent Variable | All t(p) | Idiopathic t(p) | Diabetic t(p) | Post-surgical t(p) |
|---|---|---|---|---|
| Age | −2.49 (0.001) | −1.86 (0.06) | −1.2 (0.23) | 0.28 (0.78) |
| Vb | 3.5 (<0.001) | 3.23 (0.001) | 1.79 (0.08) | 1.04 (0.31) |
| Rt | 2.61 (<0.01) | 2.35 (0.02) | −0.56 (0.57) | 1.060.3) |

Conclusion of Example XVII

Permanent GES for severe GP results in significant and sustained improvement of overall symptoms and quality of life. The independent predictors of response (age, Vb score, and Rt) were most significant in ID patients. Rt derived from endoscopic tGES mucosal EGG is an accurate predictive criterion of symptom improvement with GES, especially improvement in vomiting.

Example XVIII

Correlation of Recording from Mucosal and Serosal EGG Probes with Gastric Emptying and Gastric Neuro-Muscular Status This example examines the relationship between electrical activity generated by the Interstitial Cells of Cajal (ICC) and the number of cells in the muscle layers of the gastric wall. This relationship was studied in patients with refractory gastrointestinal motor disorders using mucosal and serosal probes placed either endoscopically in the GI lab or serosally in the Operating Room.

Procedure 29 patients (25 female, 4 male, mean age 34 years) with upper gastrointestinal motor disorders had full thickness seromuscular biopsies of the stomach at the time of gastric electrical stimulation (GES) system implantation. Immunohistochemical staining with anti-CD117 antibodies was used to identify ICC cells. The numbers of CD117 positive cells per high power field were quantified in the inner circular muscle (I) and outer longitudinal muscle (O) layers of the muscularis propria for each patient. EGG recordings were obtained from electrodes placed either endoscopically through the mucosa (M) into the inner muscle layer or surgically through the serosa (S) into the outer muscle layer at the time of placement of temporary or permanent electrical stimulation devices respectively.

The EGG data are reported as average frequency (freq) in cycles per minute, average amplitude (amp) in millivolts (mV), and as the frequency/amplitude ratio (FAR). Pair-wise correlation coefficients (r) were calculated to assess the associations between EGG values and the number of CD117 positive cells in the inner (I) and outer (O) muscle layers of the muscularis propria as well as 4-hour GET after eating a low-fat solid meal.

Results of XVIII

As shown in Table 19, mucosal amplitude correlated with the outer muscle CD117 cells and mucosal amplitude, frequency, and FAR correlated with the 4-hour GET ($p=0.05$ to 0.10 by correlation coefficients).

TABLE 19

Serosal and Mucosal EGG Correlations with ICC in Inner and Outer Muscle Layers

| | Outer muscle correlation and p value | Inner Muscle correlation and p value | GET 4 hour correlation and p value |
|---|---|---|---|
| Serosal amplitude | −0.17/0.43 | −0.07/0.74 | −0.01/0.97 |
| Serosal frequency | 0.05/0.80 | −0.01/0.97 | 0.08/0.71 |
| Serosal FAR | −0.04/0.85 | 0.02/0.91 | 0.05/0.78 |
| Mucosal amplitude | 0.32/0.10 | 0.13/0.53 | −0.33/0.09 |
| Mucosal frequency | −0.19/0.35 | −0.05/0.80 | 0.39/0.05 |
| Mucosal FAR | −0.06/0.75 | −0.05/0.82 | −0.35/0.07 |

Table 19 shows that the mucosal EGG is superior to the serosal EGG in both pre-correlating with GI neuromuscular status and also correlating with gastric emptying test values of patients, showing that the correlation of the mEGG is better than the serosal EGG in correlation with the neuromuscular status of a given patient, providing evidence that the mEGG and the FAR predict not only the neuromuscular status but also which patients may respond to temporary and permanent GES.

Conclusion of Example XVIII

In patients with refractory gastrointestinal motor disorders, the mucosal amplitude correlates with some measures of CD117 cells and the mucosal amplitude, frequency, and FAR correlates with the 4-hour GET. The data showed that the mucosal EGG correlated better with gastric emptying than the serosal EGG.

Example XIX

Double Blinded Randomized Study of Temporary Gastric Electrical Stimulation (GES): The Endo Stim Study Summary 58 patients were enrolled in this example with symptoms of gastroparesis. Eleven males and forty-seven females with a mean age of 46 years had underlying diagnoses of idiopathic gastroparesis (38), diabetic gastroparesis (13), and post-surgical gastroparesis (7).

Procedure

Baseline assessments on all patients were performed, and symptoms including vomiting, nausea, total gastrointestinal symptom score and health related quality of life were recorded. The mucosal electrograstrogram and cutaneous EGG as well as a radionuclide gastric emptying test of a low-fat meal ("GET"). A standard method of measuring GET was used by giving all subjects a low-fat meal and measuring the contents of the stomach an intervals of one, two and four hours before and after electrical stimulation. On day one, all patients had endoscopic placement of temporary electrodes for gastric stimulation near the antral body junction of the stomach. Patients were randomly assigned into ON and OFF groups in a double-blinded fashion. 28 patients had their stimulators turned ON first in the ON/OFF group, while stimulators remained off first in 30 patients in the OFF/ON group. At the end of day 4 of the study, the staff performed a second symptom assessment on all patients. At day 4, the stimulators that had been on were turned off, and the stimulators that had been off remained off, allowing for a 24-hour wash-out period, designed to eliminate any residual effects in the ON/OFF group. After the washout period, the 30 patients whose stimulators were off during the first phase in the OFF/ON group had their stimulators turned on, and the 28 patients, whose stimulators were turned on during the first phase in the ON/OFF group had their stimulators off for the remainder of the study. Both groups had their symptoms reassessed at the end of the trial, as previously performed in the first half of the study. The ON/OFF and OFF/ON programming was performed by un-blinded programmers, and neither patient nor staff knew which stimulators were on or off.

Endoscopic GES Electrode Placement

An area as close as possible to the junction of the antrum and the body of the stomach was selected using a standard 140-cm-long endoscope with a 7F accessory channel. A temporary cardiac pacing lead (model 6414-200; Medtronic) was inserted through the accessory channel. This temporary lead had an inner bipolar electrode pacing lead and an outer covering sheath, which is 120 cm long and does not exit the endoscope. The long inner lead was passed through the accessory channel and was screwed into the stomach mucosa with a clockwise corkscrew motion. The outer sheath then was removed, leaving the inner lead in place. The endoscope was withdrawn while advancing the inner lead so that it remained in position, with an extra length of at least 10 cm in the stomach. Excessive coiling of the electrode was avoided during insertion to facilitate clip attachment.

The endoscope was reintroduced to the stomach, and an endoscopic clipping device (QuickClip 2; Olympus America Corp, and/or Resolution Clip, Boston Scientific Corp) was passed through the accessory channel. Three to five clips were applied to hold the lead in place within the stomach, placing at least one clip near the distal metallic terminal part of the lead to achieve the desirable electrical impedance. The lead was connected to an external GES device (Enterra) that can be placed in a shirt pocket, a cardiac telemetry pouch, or a fanny pack, and the impedance was determined to guide the current delivered by the device. The GES device was programmed beginning with previously standardized parameters: frequency, 14 Hz; amplitude, 5 to 10 mA; pulse width, 330 microseconds; cycle ON, 0.1 to 1.0 seconds; cycle OFF, 5.0 to 4.0 seconds. These parameters were used as a starting point, with modification of parameters permitted for individual patients, based on patient intolerance, such as a shocking sensation.

In the first four days of the study, no electrodes were dislodged. In the second four days, six came out in the ON/OFF groups, and seven in the OFF/ON group. 45 of the 58 patients finished all 8 days with the electrode in place (Electrode displacement was dependent on duration of placement rather than stimulation activation).

Patients were randomized to ON/OFF or OFF/ON by a previously determined randomization table. Patients were not further sub-stratified by diagnosis, electrophysiologic, or gastic emptying characteristics at enrollment.

Patients were also evaluated by primary diagnosis and were further sub-stratified by symptoms pattern. Patient's quality of life was assessed during the study on a −3 to +3, worse to best scale for each phase of the study. Placebo effect was evaluated for the patient's historical symptoms vs. day 0 of the study. The placebo effect was determined by two techniques: (1) between baseline symptoms and Day 1; and (2) between the two groups.

A post-Hoc analysis was also performed. A group of 34 patients (from the original 58) were examined with permanent GES, with a mean follow-up of 22.4 months, to see if the randomized group effect persisted long term. The baseline factors were compared that correlated with the outcome of reduction in vomiting. All baseline characteristics were examined, including symptoms and physiologic measures versus outcome of vomiting, when the device was randomized to ON or OFF. This analysis also included an examination of the baseline mucosal EGG at the time of stimulator electrode placement. The mucosal EGG signals were analyzed by the frequency, amplitude and their ratio (FAR) using a signal averaging technique.

When the two groups ON/OFF and OFF/On were analyzed, vomiting decreased and health related quality of life (HRQOL) improved. Symptom improvement was rapid when the stimulator was on and persisted even after the stimulator was turned off in the second half of the study. See Table 20.

TABLE 20

| HRQOL Device Group | N = | Baseline | N = | Day 4 | N = | Day 8 |
|---|---|---|---|---|---|---|
| ON/OFF | 22 | −2.14 | 24 | 1.56 | 21 | −0.02 |
| OFF/ON | 23 | −2.50 | 22 | 0.32 | 17 | 0.62 |
| Between Group T-test p value | | 0.30 | | 0.02 | | 0.31 |

The baseline placebo effect was 24 percent, consistent with other severe GI disorders.

In the first 4 days, the mean number of days vomiting decreased from 1.4 with the stimulators off to 0.4 with stimulators on. Days of nausea decreased from 1.6 when the stimulators were off to 0.08 when the stimulators were on.

For the ON/OFF group, Total symptom score (TSS) decreased from a baseline mean of 12.77 to 5.8, after 4 days with the stimulator turned on. After the washout period and the following additional days of the stimulator turned off, the TSS increased from 5.8 to 7.4, but not back to the patient's baseline of 12.77, suggesting a possible carry-over effect from prior stimulation during the first four days of the study. Of the 27 patients on the ON/OFF group, 44 percent were vomiting on day one. By day three, only seven percent were vomiting. Of the 30 patients in the OFF/ON group, 36 percent were vomiting on day six, compared to 30 percent by day eight (Table 21).

TABLE 21

|  | Day 1 | Day 2 | Day 3 | Day 4 | Day 5 | Day 6 | Day 7 | Day 8 |
|---|---|---|---|---|---|---|---|---|
| Temp ON for the First 4 days and Then OFF for Last 4 Days ||||||||||
| Total Patients | 27 | 28 | 28 | 28 | 25 | 23 | 23 | 22 |
| # Vomiters | 12 | 7 | 2 | 3 | 7 | 6 | 8 | 6 |
| % Vomiters | 44 | 25 | 7 | 11 | 28 | 26 | 35 | 27 |
| Temp OFF for the First 4 days and Then ON for Last 4 Days ||||||||||
| Total Patients | 30 | 30 | 30 | 30 | 28 | 25 | 25 | 23 |
| # Vomiters | 16 | 13 | 15 | 14 | 10 | 9 | 9 | 7 |
| % Vomiters | 53 | 43 | 50 | 47 | 36 | 36 | 36 | 30 |
| p-value | 0.50 | 0.14 | 0.0003 | 0.003 | 0.55 | 0.46 | 0.93 | 0.82 |

GET at baseline was measured on day four and day eight. There was no change in GET for all patients as a group. There was a slight improvement in 4 hour GET for the patients with delayed GET, but it was not significant. There was also a slight p . . . in 1 hour GET in the non-delayed Group. This also was not statistically significant.

TABLE 22

TEMP GES: Effect on All Study Patients

| Day | 1 Hr Base | Day 4 | Day 8 | 4 Hr Base | Day 4 | Day 8 |
|---|---|---|---|---|---|---|
| OFF/ON (n = 30) | 66.1 | 62.3 | 68.6 | 16.4 | 21.8 | 20.3 |
| ON/OFF (n = 27) | 67.1 | 69.9 | 64.7 | 24.7 | 24.1 | 24.7 |

TABLE 23

Temp GES: Effect on Patients with Delayed GET

| Day | 1 Hr Base | Day 4 | Day 8 | 4 Hr Base | Day 4 | Day 8 |
|---|---|---|---|---|---|---|
| OFF/ON (n = 10) | 83.7 | 82.4 | 74.8 | 38.6 | 46.3 | 36.3 |
| ON/OFF (n = 16) | 77.5 | 77.9 | 75.7 | 38.0 | 35.4 | 40.9 |
| p value | 0.34 | 0.58 | 0.91 | 0.96 | 0.41 | 0.75 |

TABLE 24

Temp GES: Effect on Patients with Non-Delayed GET

| Day | 1 Hr Base | Day 4 | Day 8 | 4 Hr Base | Day 4 | Day 8 |
|---|---|---|---|---|---|---|
| OFF/ON n = 20 | 57.4 | 51.7 | 65.0 | 4.1 | 8.9 | 10.6 |
| ON/OFF n = 11 | 51.9 | 60.0 | 52.6 | 5.4 | 10.0 | 6.9 |
| p value | 0.52 | 0.35 | 0.12 | 0.28 | 0.69 | 0.45 |

Cutaneous EGG Cutaneous EGG was measured at baseline, on day four, and day eight; analyzed by signal averaging for frequency and amplitude; stratified by low or high EEG; and analyzed using paired T-tests. The most consistent effects were in the ON/OFF group. Non-stratified EGG decreased on day four then increased in frequency on day eight. Low EGG increased when the stimulator was on, while high EGG decreased when the stimulator was on ($p \leq 0.05$). See Table 25.

TABLE 25

Temp GES Effect on EGG

| Group Day | Base | ON/OFF n = 28 Day 4 | Day 8 | Base | OFF/ON n = 30 Day 4 | Day 8 |
|---|---|---|---|---|---|---|
| All (n = 58) | 4.56 | 4.04 | 5.10 | 4.04 | 4.40 | 4.39 |
| p | — | 0.21 | 0.20 | — | 0.42 | 0.87 |
| Low (n = 14) | 2.4 | 4.4 | 3.6 | 2.3 | 4.5 | 4.1 |
| p | — | 0.05 | 0.06 | — | | |
| High (n = 44) | 5.16 | 4.0 | 5.2 | 4.5 | 4.35 | 4.48 |
| p | — | <0.01 | 0.48 | — | 0.58 | 0.81 |

Mucosal EGG was measured at the time stimulators were implanted, mucosal EGG measurement correlated with vomiting on day four. It was calculated as the ratio frequency to amplitude and correlated with symptoms. Mucosal EGG had a much higher correlation with symptoms than cutaneous EGG. A later, post-hoc analysis revealed that the frequency/amplitude ratio for the two groups was not equal. The ON/OFF groups had lower, and more normal FAR than the OFF/ON group (Table 26). Means and SDs of data collected by OFF_ON (Period1=OFF) and ON_OFF (Period1=ON) were examined using the MEANS procedure with 3 criteria found to be significant: Vperm 0.72±1.29 in the ON_OFF group vs. 1.98±1.53 in the OFF_ON group (p=0.01), TSSperm 8.66±5.87 in the ON_OFF group vs. 13.30±5.00 in the OFF_ON group (p=0.01) and F/A Ratio 6.59±4.86 in the ON_OFF group vs. 19.65±27.41 in the OFF_ON group (p=0.02).

TABLE 26

Double Blind Permanent Data by OFF/ON Groups

| Measure | ON_OFF Group | OFF_ON Group | P-value |
|---|---|---|---|
| Vperm | 0.72 ± 1.29 | 1.98 ± 1.53 | P = 0.01 |
| TSSperm | 8.66 ± 5.87 | 13.30 ± 5.00 | P = 0.01 |
| F/A Ratio | 6.59 ± 4.86 | 19.65 ± 27.41 | P = 0.02 |

When stratified into three patient groups according to the etiology of gastroparesis (whether diabetic gastroparesis, post-surgical gastroparesis, or idiopathic gastroparesis), the patients with diabetic gastroparesis had the greatest improvement in symptoms, with vomiting scores decreasing from 0.83 to 0.00 and total symptom scores decreasing from 5.17 to 1.83, when reassessed after four days with the stimulator turned on. Regardless of the etiology of gastroparesis, there was a 70-80 percent improvement in vomiting scores after the first four days of stimulation in the ON/OFF groups. In the idiopathic gastroparesis group, vomiting scores went from a baseline of 1.24 to 0.33, after four days of stimulation, but returned to only 0.38 after four days of being turned off, suggesting a persistent anti-emetic effect from prior stimulation during the first four days, and/or the result of differences in mucosal EGG measured frequency, amplitude or ratio (FAR) between the 2 groups. If the OFF/ON groups, all etiologies of gastroparesis had improvement in vomiting scores of 40-50 percent with gastric stimulators initially being off in the first half of the study and turned on for the second half (Tables 27, 28 and 29).

TABLE 27

Diagnosis ON vs. OFF: Idiopathic

| Group | Vomiting OFF/ON n = 20 | (0-4) ON/OFF n = 18 | TSS OFF/ON n = 20 | (0-20) ON/OFF n = 18 |
|---|---|---|---|---|
| Day 1 | 1.4 | 1.24 | 8.48 | 8.82 |
| Day 4 | 1.15 | 0.33 | 7.40 | 7.31 |
| Day 8 | 0.67 | 0.38 | 6.67 | 7.77 |

TABLE 28

Diagnosis ON vs. OFF: Diabetes

| Group | Vomiting OFF/ON n = 7 | (0-4) ON/OFF n = 6 | TSS OFF/ON n = 7 | (0-20) ON/OFF n = 6 |
|---|---|---|---|---|
| Day 1 | 1.29 | 0.83 | 7.43 | 5.17 |
| Day 4 | 2.0 | 0.00 | 8.71 | 1.83 |
| Day 8 | 0.6 | 2.20 | 5.8 | 5.6 |

TABLE 29

Diagnosis ON vs. OFF: Post Surg

| Group | Vomiting OFF/ON n = 3 | (0-4) ON/OFF n = 4 | TSS OFF/ON n = 3 | (0-20) ON/OFF n = 4 |
|---|---|---|---|---|
| Day 1 | 0.67 | 1.75 | 9.67 | 9.5 |
| Day 4 | 1.33 | 0.50 | 11.67 | 7.75 |
| Day 8 | 0.67 | 0..25 | 5.0 | 6.25 |

Twenty patients in the study had a cyclic/episodic symptom pattern. These patients had a greater deterioration of symptoms when stimulation was deactivated/OFF, and patients with non-cyclic symptoms had a greater improvement when stimulation was activated (Tables 30 and 31). These differences may provide clues to the mechanisms by which stimulation is helpful.

TABLE 30

Sx Pattern & TempGES: Off/On

| Status Day | Vomit Base Day 1 | (0-4) Off Day 4 | On Day 8 | TSS Base Day 1 | (0-20) Off Day 4 | On Day 8 |
|---|---|---|---|---|---|---|
| Cyclic n = 11 | 1.27 | 2.09 | 1.14 | 8.32 | 9.36 | 6.0 |
| NonCycn = 19 | 1.32 | 0.95 | 0.44 | 8.37 | 7.42 | 6.38 |

TABLE 31

Sx Pattern & TempGES: On/Off

| Status Day | Vomit Base Day 1 | (0-4) On Day 4 | Off Day 8 | TSS Base Day 1 | (0-20) On Day 4 | Off Day 8 |
|---|---|---|---|---|---|---|
| Cyclic n = 9 | 1.00 | 0.44 | 0.86 | 7.33 | 6.11 | 8.29 |
| NonCycn = 19 | 1.33 | 0.21 | 0.73 | 8.50 | 6.24 | 6.40 |

Discussion of Example XIX

This example was the first double-blind, randomized, placebo controlled investigation of temporary endoscopic mucosal gastric stimulation. Gastroparesis may be under-recognized in clinical practice, and patients whose gastroparesis is untreated often have a poor quality of life. The anti-emetic drugs currently available are costly and are often not effective. Prior studies have proven that permanent GES is effective and is a long-term means of alleviating the symptoms of gastroparesis. However, permanent GES requires a surgical procedure and anesthesia, and some gastroparesis patients are not good surgical candidates due to underlying complex health problems. We have shown that if a patient is thought to be a good surgical candidate, temporary GES may be used as a means of determining if a patient will benefit from permanent GES placement. Therefore, temporary GES can benefit select patients and can be used to select out patients who can avoid unnecessary surgery if the patient doesn't respond to temporary GES.

Example XX

Gastric Electrical Stimulation is Associated with Improvement in Pancreatic Exocrine Function in Humans Procedure Fecal elastase values were compared in 2 patient groups: (1) GES devices ON and (2) GES devices OFF and in 3 control groups: (1) no response (NR) to prokinetic medications, (2) positive response (RES) to medications, and (3) normal controls. Polypeptide levels in 7 of 9 GES patients with device ON and OFF, elastase results, GI symptoms (TSS), and heart rate variability (HRV) were compared by paired t tests and/or ANOVA and reported as mean±SE.

Results of Example XX

Elastase was different for GES-ON and OFF (508.0±92.2 vs. GES-OFF 378.6±87.4, P<0.05). Elastase was lower in medication NR and RES than in normal controls. Postprandial pancreatic polypeptide was greater with GES ON than OFF (P=0.07). HRV revealed a lower percentage of change with device ON versus OFF (44.2±5.5 vs. 48.5±5.2, P=0.08) and lower TSS with ON versus OFF (15.9±4.5 vs. 25.7±5.3, P<0.05).

Conclusion of Example XX

GES improves exocrine pancreatic release, effects autonomic control, and improves GI symptoms, providing evidence that GES is effective in the treatment of pancreatic insufficiency associated with gastroparesis.

Example XXI

Long-Term Follow Up of a Previous Double Masked Temporary GES Study: The Importance of Baseline Physiologic Measures Procedure This example studies a subset of 34 consecutive patients (from the original 58) to see if the randomized group effects persisted long term. Originally studied 58 patients (11 males, 47 females, mean age 46 years) with the symptoms of gastroparesis (GP) and underlying diagnosis: (idiopathic (ID), n=38; diabetes mellitus (DM), n=13; post-surgical (PS), n=7) in a randomized placebo-controlled study of tGES. The tGES was switched from ON to OFF in one group and OFF to ON in a second group during two consecutive four day sessions. Subsequently examined were a subset of 34 patients (from the original 58) who later underwent permanent GES, with a mean follow-up of 22.4 months, to see if the randomized group effect persisted long term. All baseline characteristics were examined, including symptoms and physiologic measures and vomiting outcome score, and compared the ON/OFF group (Session 1=ON, Session 2=OFF) to the OFF/ON group (Session 1=Off, Session 2=ON). Means and standard deviations were compiled by patient group: OFF/ON and ON/OFF.

Results of Example XXI

Significant group differences were found for 3 outcomes following permanent stimulation: vomiting, mean±SD=0.72±1.29 in the ON/OFF group vs. 1.98±1.53 in the OFF/ON group (p=0.01), Total Symptom Score=8.66±5.87 in the ON/OFF group vs. 13.30±5.00 in the OFF/ON group (p=0.01) and endoscopic mucosal EGG Frequency/Amplitude (F/A) Ratio=6.59±4.86 in the ON/OFF group vs. 19.65±27.41 in the OFF/ON group (p=0.02).

TABLE 32

Permanent Data by Double Masked Off & ON Groups

| Measure | ON/OFF Group | OFF/ON Group | P-value |
|---|---|---|---|
| Vperm | 0.72 ± 1.29 | 1.98 ± 1.53 | P = 0.01 |
| TSSperm | 8.66 ± 5.87 | 13.30 ± 5.00 | P = 0.01 |
| F/A Ratio | 6.59 ± 4.86 | 19.65 ± 27.41 | P = 0.02 |

Conclusion of Example XXI

Although a definitive randomization plan was used to assign patients to groups, the differences in long-term outcomes may be due in part to group differences in physiologic characteristics at baseline. Based on the data collected, the greatest improvements were in vomiting and quality of life. Symptom improvement was rapid when the device was ON for three days. Stimulation ON appears to persist once OFF for another 2 to 3 days.

A 24% placebo effect from baseline to Day 1 was independent of ON/OFF status. The 24% placebo effect is consistent with other severe GI disorders.

The results of this example provide evidence of patients who will benefit most from tGES.

Example XXII

An Energy Algorithm Improves Symptoms in Some Patients with Gastroparesis and Treated with Gastric Electrical Stimulation Procedure The relationship between GI symptoms and stimulation parameters was examined in a group of drug-refractory gastroparesis patients. From approximately 200 patients consented from 1995 to 2005 at 3 centers in the US mid-south (Memphis, Tenn.; Little Rock, Ark.; and Jackson, Miss.), 22 patients were examined (approximately 10% of the patients consented), who did not respond optimally to initial GES settings. Patients were: 5 male 17 female, mean age 35 years with underlying diagnosis: 12 with idiopathic disease (ID), 4 with diabetes mellitus (DM), and 6 post-surgical (PS) patients had GES implanted under a variety of research and clinical protocols. Patients were all refractory for drug treatment of gastroparesis at baseline and had gastric electrical stimulators placed under the terms of the specific protocol. Most required the demonstration of drug-refractoriness and disordered gastric emptying in addition to chronic nausea and vomiting for eligibility.

Patients were seen for follow-up in a standardized manner: 3, 6, 12 months after implant and then at least every 12 months, patients were seen more often if clinically indicated, and had both symptom assessment and device interrogation at each visit. For patients whose symptoms had not responded optimally to initial stimulation (which was determined subjectively for each patient) an algorithm approach to changing GES parameters was offered. For patients implanted prior to April 2000, the stimulation parameters were not varied from baseline, as required by the FDA protocol at the time. Beginning in the spring of 2000, all patients seen were offered the algorithm, which is described in the next paragraph. Thus, the time of initiation of the algorithm was dependent on when the device was implanted. For example, a patient implanted in 1997, and who did not respond optimally, would not have begun the algorithm until after May, 2000. Likewise, a patient implanted in 2002, but who also did not respond optimally, could have begun the algorithm as soon as 3 months post implant.

First, patients were evaluated, via a structured algorithm, stimulation parameters delivered in order to obtain optimal (lowest) symptoms, by GI Total Symptom Score [TSS] (nausea, vomiting, bloating, anorexia, and abdominal pain as TSS, maximum score 20).

The algorithm made changes in stimulation parameters in the following order: increased current, then increased on time (duty cycle) and lastly, frequency. Once a change was made— for example—an increase in current that change remained while the next change—for example in on timecycle, was made. All patients used the same algorithm and changes were made in the order specified. Once a patient reached symptom control that was satisfactory for that patient, the algorithm was not used further and each patient was left at the latest stimulation parameter.

The mean time of stimulation since algorithm application was 4.2 months. Since the stimulation parameters which resulted in improved symptom scores for each patient were different, the data was analyzed by computing: charge per pulse, energy per pulse, and average power for each patient. These were estimated, first with the standard clinical settings, and then after application of the algorithm. The formulas used for these calculations are in Table 33.

TABLE 33

Formulas Used for Energy Parameters (adapted from reference 10)

| | Formula |
|---|---|
| Duty Cycle (DC) | Frequency × Pulse Width × (On Time/(ON Time + Off Time)) |
| Charge (micro-Coulomb) | Current × Pulse Width |
| Average Power (micro-Watt) | Current$^2$ × Impedance × DC |
| Energy/Pulse (micro-Joule) | Current$^2$ × Impedance × Pulse Width |

IMPEDANCE & POWER VALUES
Standardized Parameters
Amplitude(current) = 0.005 A
Frequency = 14 HZ
Pulse Width = 0.00033 Sec
On Time = 0.1 Sec
Off Time = 5 Sec Standardized Parameters
Amplitude (current)=0.005 A
Frequency=14 HZ
Pulse Width=0.00033 Sec
On Time=0.1 Sec
Off Time=5 Sec The energy values were compared by the 3 diagnostic subgroups: ID, DM, PS to examine any differences, after algorithm application, existing between sub-groups and compared these by analysis of variance (ANOVA).

Results of Example XXII

Compared to baseline, GI Total Symptoms Scores improved in the patients undergoing the algorithm as did energy values, listed as mean values in the Table 22. Using the algorithm, 18 of the 22 patients were able to achieve at least a 50% improvement in symptoms from baseline. The average TSS change from baseline with standard parameters was 36% (pre-algorithm) and the average change from baseline to optimal parameters was 59% (post-algorithm). No patients appeared to have worsening on symptoms from changes made with the algorithm, although some patients (approximately 10%) did not improve with any given change. Significant differences existed for most energy parameters, but the differences for current, charge per pulse, and energy per pulse were the most significantly different as noted in the

TABLE 34

Mean values for all patients before and after the algorithm

| | Current (ohms) | Charge/Pulse (coulombs) | Charge On T (coulombs) | Energy/Pulse (joules) | Energy On T (joules) | Power (watts) | TSS |
|---|---|---|---|---|---|---|---|
| Baseline (before implant) | Na | Na | Na | Na | Na | Na | 15.62 |
| Mean before implant (std parameters) | 5.5E−03 | 1.8E−06 | 3.6E−06 | 5.6E−06 | 1.1E−06 | 1.6E−06 | 10.17 |
| Mean after algorithm | 7.0E−03 | 2.3E−06 | 2.5E−05 | 8.6E−06 | 1.0E−04 | 1.4E−05 | 6.7 |
| p value | 0.03 | 0.03 | 0.03 | 0.06 | 0.02 | 0.04 | 0.02 |

Comparison of energy values by diagnostic subgroups for each of the 3 diagnostic groups: rD, DM and PS showed that the patients in the PS subgroup required statistically greater amounts of energy than the other groups, compared by ANOVA, as noted in Table 35.

TABLE 35

Average values for various sub-groups leading to lowest TSS

| SubG Avg | Current (ohms) | Charge/Pulse (coulombs) | Charge On T (coulombs) | Energy/Pulse (joules) | Energy On T (joules) | Power (watts) | TSS Before | TSS After |
|---|---|---|---|---|---|---|---|---|
| DM | 6.9E−03 | 2.3E−06 | 4.5E−06 | 9.0E−06 | 1.8E−05 | 2.5E−06 | 19 | 6.4 |
| ID | 6.4E−03 | 2.1E−06 | 2.8E−05 | 6.5E−06 | 9.8E−05 | 8.2E−06 | 15 | 6 |
| PS | 8.1E−03 | 2.7E−06 | 2.6E−05 | 1.2E−05 | 1.4E−04 | 2.6E−05 | 14 | 6.9 |

Discussion of Example XXII

Figure 12:
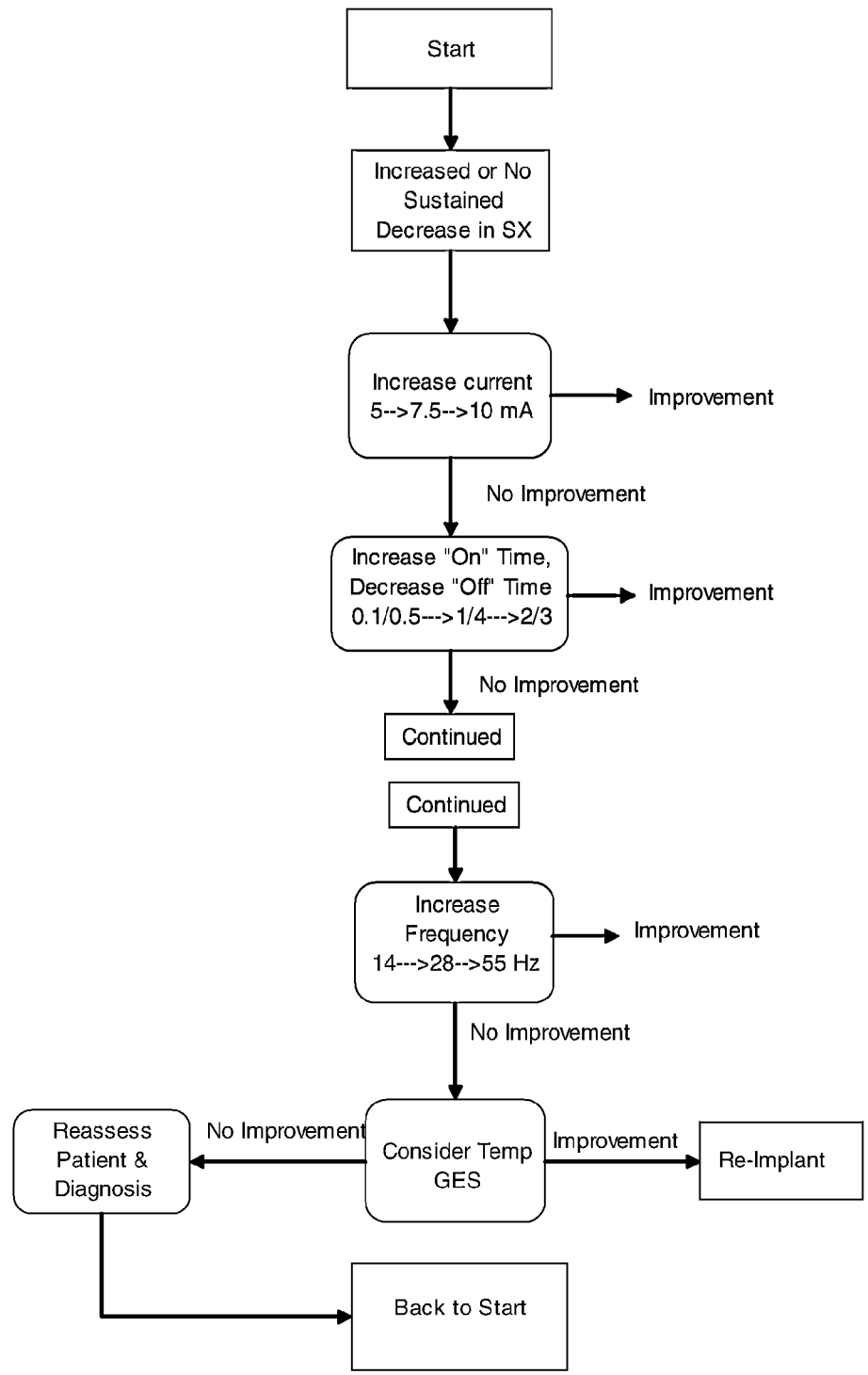
FIG. 12 is a flow chart depicting an algorithm for GES symptom improvement, in accordance with the present invention.
Figure 13:
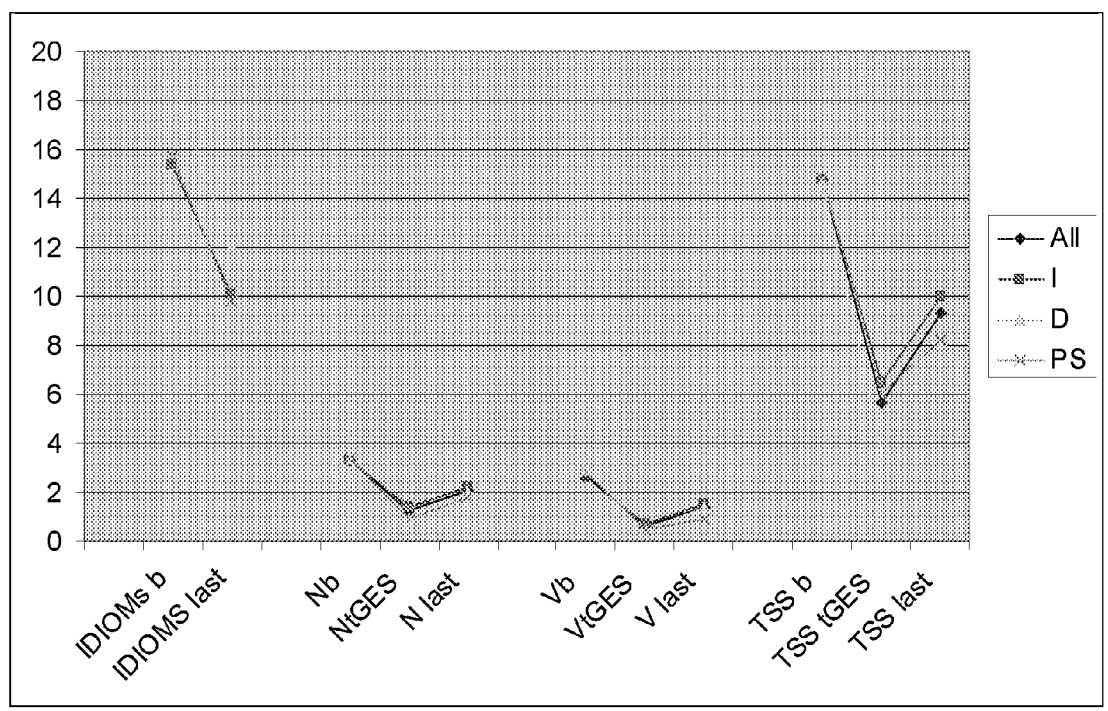
FIG. 13 shows that the FAR (or Rt=ratio of temp) predicts response to GES, in accordance with the present invention, where far is abbreviated by another term rt (ratio of the temp stim—meaning the far measured when a temp stim is being placed.

In this study, an algorithmic approach was used to varying GES parameters with the objective of achieving maximum symptom suppression in each patient. See, e.g., FIG. 12, which is a flow chart depicting the algorithm used. The algorithm was patient symptom driven—that is, when a patient was seen for follow-up, if the patient's symptom control was satisfactory, no changes in stimulation were made. Reported here are the initial results, illustrating that stimulation parameters, which result in improved symptoms, may vary from patient to patient, and may be different depending on the etiology of gastroparesis.

A number of types of stimulation are currently used for electrical stimulation of the gut. The two main types of stimulation used are first: high energy with low frequency (sometimes called gastric pacing) and second: low energy with high frequency stimulation, as used in this application. A complete discussion of the types of electrical stimulation used has been done elsewhere, but the focus of this study was low-energy (in micro-volts) and high frequency (generally about 4 times the physiologic gastric frequency) stimulation.

The mechanism of the positive effects of gastric electrical stimulation remains unknown. Not being bound to one theory, several exist. These include direct effect on muscle, effects on amplitude or frequency of the gastric slow wave, and effects on efferent or afferent nerves, other mechanisms, including central mechanisms, that are hypothesized to improve the symptom complex knows as gastroparesis. Similar algorithmic based variation done with thalamic stimulation has shown the importance to affect symptom outcome.

Not all patients respond equally to GES. It was found that 18/22 of patients who did not initially respond optimally with standard stimulation parameters achieved at least a 50% improvement from pre-implant TSS levels after changing stimulation parameters using the algorithmic approach. Since the average change in symptoms was less than 50% pre-algorithm and greater than 50% post algorithm, it is advisable to use this algorithm before abandoning GES in a given patient.

In addition to the 22 patients as a whole, this study also looked at patients by diagnostic subgroups. Although the subgroups were relatively small, some differences were found, the post-surgical patients required the most energy to maintain symptom improvement.

Based on the results of a symptom-driven GES energy algorithm, that changes in stimulation parameters for GES can be associated with improvements in symptoms. Stimulation parameters resulting in maximum symptomatic improvement can vary from patient to patient in the treatment of gastroparesis with GES. Further use of an algorithmic approach may help guide parameters used for GI electrical stimulation for optimal symptom reduction in specific patients.

CASE Studies

The following 20 case studies provide examples of implementation of the present method.

Case Study I: Transplant Related Disorders

1. Typical case—

The patient is a 38 year old white male with long standing diabetes mellitus and a history of short gut syndrome on a neo-natal basis and a recent combined pancreas and small bowel treatment but patient has been able to be discharged from the hospital as he as can not keep his immunosuppressants down.

2. How Mucosal EGG can be performed—

At the time of one of his many EGDs.

3. How FAR can be used from EGG—

To show that the cause of the main GI problems may be disordered neuro-muscular function.

4. How tGES can be used—

To enable patient to keep his oral meds down. A wireless GES device is let in place in the gastric pouch near the anastamosis.

Case Study II: Autonomic and Neurologic Disorders

1. Typical case—

The patient is a 27 year old with an inherited autonomic disorder with associated upper, mid and lower GI symptoms. Patient has been refractory to all meds and other prescriptions.

2. How Mucosal EGG can be performed—

Endoscopically.

3. How FAR can be used from EGG—

To demonstrate the combination of autonomic and enteric dysfunction.

4. How tGES can be used—

To stabilize ANS and ENS function. Once shown, a intermediate term wireless endoscopic or long term serosal device can be placed.

Case Study III: Bacterial Overgrowth and Small Bowel Dysmotility

1. Typical case—

A 53 year old white female is bothered by refractory bloating and distension. A hydrogen breath test shows bacterial overgrowth but the patient has had only minimal response to a non-absorbable antibiotic.

2. How Mucosal EGG can be performed—

Of small bowel at the time of aspirate of contents of the small bowel, for microbiologic analysis. The mEGG is done in the small bowel.

3. How FAR can be used from EGG—

To confirm a likely neuro-muscular abnormality without a full thickness biopsy.

4. How tGES can help—

If patient responds to a trial of tGES I the small bowel, a longer term wireless device may be indicated.

Case Study IV: Classic Eating Disorders

1. Typical case—

A 24 year old Hispanic female was diagnosed with anorexia nervosa at age 13. She has lingered for years with borderline weight and recently returned with her family from a well known hospital where enforced eating did not improve her weight. Her GET has shown delayed emptying for years.

2. How Mucosal EGG can be performed—

Via EGD.

3. How FAR can be used from EGG—

To demonstrate intrinsic electrical dysrhythmias of the stomach.

4. How tGES can be used—

To help the patient regain weight and remodel her gastric motor function.

Case Study V: Constipation, Diarrhea, Pelvic Floor Disorders

1. Typical case—

A 43 year old African-American female has refractory symptoms, including alternating constipation and diarrhea. A pelvic floor evaluation indicated no gross anatomic abnormality, and only muscular weakness. A trial of pelvic floor rehab was not helpful.

2. How Mucosal EGG can be performed—

Via the colonoscope the m EGG can be preformed.

3. How FAR can be used from EGG—

To indicate if neural stimulation might be helpful.

4. How tGES can be used—
Prior to a permanent device.
Case Study VI: Cyclic Vomiting Syndrome
1. Typical case—
A 17 year old white female has had many years of episodes of cyclic nausea and vomiting. No interventions have been helpful.
2. How Mucosal EGG can be performed—
Can be measured during one of many admissions requiring endoscopy.
3. How FAR can be used from EGG—
A relatively normal FAR may indicate a trial of GES is warranted.
4. How tGES can be used—
To interrupt the pattern of cyclic vomiting and prevent further occurrences.
Case Study Vii: Diabetes and Other Metabolic Disorder
1. Typical case—
A 47 year old obese white female has difficulty maintaining good blood sugar control despite intensive insulin therapy. Upper gut symptoms were minimal but the patient did have cyclical episodes of severe nausea, especially in the morning. GET was minimally delayed at 1 and 2 hours on a 4 hour meal. The 4 hour measure was normal.
2. How Mucosal EGG can be performed—
Endoscopically, often showing an abnormality.
3. How FAR can be used from EGG—
To predict that patient's gastric function might be improved.
4. How tGES can be used—
As a trial before consideration of a permanent device. A prolonged wireless endoscopic device may be of use as well.
Case Study VIII: Hyperemesis
1. Typical case—
21 year old, 32 week pregnant patient who has trouble maintaining nutrition and has required TPN to maintain her weight. She has been hospitalized for 12 weeks.
2. How Mucosal EGG can be performed—
Via EGD done for persistent vomiting.
3. How FAR can be used from EGG
If normal, patient's chance of recovery from HE is good.
4. How tGES can be used—
To enable the patient to stop TPN prior to delivery.
Case Study IX: Nausea/Vomiting of any Etiology
1. Typical case—
23 year old female with idiopathic nausea/vomiting but normal GET. However, compromised nutrition has resulted in weight loss.
2. How Mucosal EGG can be performed—
Measured at the time of EGD—showed markedly abnormal FAR suggestive of a neuromuscular disorder.
3. How FAR can be used from EGG—
To guide treatment: a trial of endoscopic tGES.
4. How tGES can be used—
To see if patient responds—if so: permanent GES.
If not—full-thickness biopsy at time of feeding tube placement
Case Study X: NV of Chemotherapy
1. Typical case—
68 year Asian female who is suffering her second recurrence of breast cancer. Recent radiation has left her with chronic nausea and vomiting and inadequate nutrition associated with poor quality of life. Oral medications have not been helpful in part because the medications won't stay down.
2. How Mucosal EGG can be performed—
Via EGD at time of feeding tube placement to augment nutrition.
3. How FAR can be used from EGG—
FAR was moderately abnormal indicating that patient might benefit from tGES.
4. How tGES can be used—
As a trial to see if patient's nutrition, symptoms and quality of life can be improved.
Case Study XI: Pancreatitis
1. Typical case—
44 year old African-American male with history of alcohol induced pancreatitis. Pain and adequate nutrition are issues that are on going.
2. How Mucosal EGG can be performed—
At time of an EGD, the mEGG indicated a high FAR due to moderately high frequency and very low amplitude.
3. How FAR can be used from EGG—
To indicate that tGES may help the patient.
4. How tGES can be used
As a trial to see if patient's nutrition can be improved.
Case Study XII: Pancreato-Biliary Disorders
1. Typical case—
54 year old white female with history of biliary pain and a previous diagnosis of biliary dyskinesia. An endoscopic sphincterotomy has not relieved her symptoms.
2. How Mucosal EGG can be performed—
At time of an ERCP, the mEGG indicated a high FAR due to moderately high frequency and very low amplitude.
3. How FAR can be used from EGG—
To indicate that tGES may help the patient.
4. How tGES can be used
As a trial to see if patient's biliary pain can be relieved.
Case Study XIII: Post-Surgical Disorders
1. Typical case—
A 73 year old white male had peptic ulcer surgery 40 years ago. Since then he had chronic GI distress which has limited his nutrition.
2. How Mucosal EGG can be performed
Endoscopically.
3. How FAR can be used from EGG—
To demonstrate a denervated gastric pouch
4. How tGES can be used—
To show that GES will be the best treatment for this patient.
Case Study XIV: Rapid and Other Disordered Gastric Emptying
1. Typical case—
A 37 year old white male has problems with dyspepsia and postprandial diarrhea. A GET showed rapid emptying. The patient has not found any response from medications or dietary changes.
2. How Mucosal EGG can be performed—
At the time of EGD an EGG done in the mucosa indicated high frequency but also high amplitude but a low FAR.
3. How FAR can be used from EGG—
Suggesting that patient might respond to tGES.
4. How tGES can be used.
To confirm the above.
Case Study XV: Retraining of the Stomach
1. Typical case—
88 year old white female with chronic dyspepsia since a prolonged hospitalization at age 84.
2. How Mucosal EGG can be performed—
Endoscopically, when a PEG is placed.
3. How FAR can be used from EGG—
To demonstrate normal intrinsic function.
4. How tGES can be used—
To remodel the stomach. The patient may not need further GES therapy.

Case Study XVI: Detection/Diagnosis of Device Malfunction
1. Typical case—
Previously implanted GES may not be working well.
2. How Mucosal EGG can be performed—
Endoscopically, when a PEG is placed.
3. How FAR can be used from EGG—
Predict is device and/or leads are the problem.
4. How tGES can be used—
For detection/diagnosis and, if needed, direct reimplantation.
Case Study XVII: Dyspepsia
1. Typical case—
43 year old with chronic dyspepsia without classic GP.
2. How Mucosal EGG can be performed—
Endoscopically.
3. How FAR can be used from EGG—
To predict response.
4. How tGES can be used—
To make a decision about a more permanent device.
Case Study XVIII: GERD
1. Typical case—
35 year old with refractory hoarseness and has failed all available medical and surgical therapies.
2. How Mucosal EGG can be performed—
Endoscopically.
3. How FAR can be used from EGG—
To predict response to temp Stim.
4. How tGES can be used—
To consider permanent GES.
Case Study XIX: GP
1. Typical case—
Patient with screoderman, but not sure if permanent GES would help.
2. How Mucosal EGG can be performed—
Endoscopically.
3. How FAR can be used from EGG—
To predict response to permanent GES.
4. How tGES can be used—
To make a decision about permanent GES.
Case Study XX: Other Neuromuscular Disorders
1. Typical case—
18 year old with cerebral palsy requiring a feeding tube despite normal intellectual and school functioning.
2. How Mucosal EGG can be performed—
Via PEG at time of changing of PEG tube.
3. How FAR can be used from EGG—
To evaluate neuromuscular status.
4. How tGES can be used—
Via PEG and mucosal stimulation.
Case Study XXI: Inability to Lose Weight (Refractory Obesity)
1. Typical case—
32 year old white female with lifelong weight problems: nothing has been able to work for the patient. She was recently declined for a gastric bypass procedure.
2. How Mucosal EGG can be performed—
Via routine endoscopy mucosal EGG can be measured, along with autonomic measures.
3. How FAR can be used from EGG—
To indicate if mucosal tGSE might help this patient normalize her weight.
4. How tGES can be used—
tGES can indicate if gastric neuromodulation might help this patient.
Case Study XXII: Diabetes and Other Metabolic Disorders, Including Low Blood Sugar
1. Typical case—
A 47 year old obese white female has difficulty maintaining good blood sugar control despite intensive insulin therapy. Upper gut symptoms were minimal, but the patient did have cyclical episodes of severe nausea, especially in the morning. GET was minimally delayed at 1 and 2 hours on a 4 hour meal. The 4 hour measure was normal.
2. How Mucosal EGG can be performed—
Through the endoscope, often showing an abnormality.
3. How FAR can be used from EGG—
To predict that patient's gastric function might be improved.
4. How tGES can be used—
As a trial, before consideration of a permanent device. A prolonged wireless endoscopic device may be of use as well.

The present invention thus being described, it would be obvious that the same can be varied in many ways. Such variations that would be obvious to one of ordinary skill in the art is to be considered as being part of this disclosure.

Unless otherwise indicated, all numbers expressing quantities, specifically amounts set forth when describing experimental testing, are to be understood as being modified in all instances by the term "about." Accordingly, unless indicated to the contrary, the numerical parameters set forth in the Specification and Claims are approximations that may vary depending upon the desired properties sought to be determined by the present invention.

Additionally, notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

This application has references cited herein. All such references, included those listed below, are incorporated herein by reference in their entirety.

REFERENCES

1. Kendall B J, McCallum R W. Gastroparesis and the current use of prokinetic drugs. Gastroenterologist 1993; 1:107-114.
2. Abell T L, Camilleri M, Hench V S, Malagelada J-R. Gastric electro-mechanical function and gastric emptying in diabetic gastroparesis. Eur J Gastroenterol Hepatol 1991; 3:163-167.
3. Feldman M, Smith H J. Effect of cisapride on gastric emptying of indigestible solids in patients with gastroparesis diabeticorum: a comparison with metoclopramide and placebo. Gastroenterol 1987; 92:171-174.
4. Janssens J, Peeters T L, Vantrappen G et al. Improvement of gastric emptying in diabetic gastroparesis by erythromycin. NEJM 1990; 322:1028-1031.
5. Soykan I, Sarosiek I, McCallum R W. The effect of chronic oral domperidone therapy on gastrointestinal symptoms, gastric emptying and quality of life in patients with gastroparesis. Am J Gastroenterol 1997; 92: 976-980.
6. McCallum R W, Chen J D, Lin Z et al. Gastric pacing improves emptying and symptoms in patients with gastroparesis. Gastroenterol 1998; 114:456-461.
7. Luo j, Abell T L. Gastric electrical stimulation improves both GI symptoms and gastric emptying in patients with "post-surgical" gastroparesis. Gastroenterol 1999; 116: S0162.

8. Familoni, B O, Abell, T L et al. Electrical stimulation at a frequency higher than basal rate in human stomach. Dig Dis Sci 1997; 42: 885-891.
9. Abell T, McCallum R, Hocking, M, Koch, K, Abrahamsson, H, et al. Gastric electrical stimulation for medically refractory gastroparesis. Gastroenterol 2003; 125:421-428.
10. Abell T L, Cutsem V E. Gastric electrical stimulation in intractable symptomatic gastroparesis. Digestion 2002; 66:204-212.
11. Abell T L, Malagelada, J R. Glucagon evoked gastric dysrhythmias in healthy humans demonstrated by an improved electrogastrographic method. Gastroenterol 1984; 86:1011.
12. Ayinala S R, Goyal A, Khurana I S, Bhragava S I, Familoni B, Abell T L. Response to gastric electrical stimulation performed with temporary electrodes corresponds well to permanent implantation. Neurogastroenterol Motility 2002; 14: 422.
13. Hasler W L. The brute force approach to electrical stimulation of gastric emptying: A future treatment for refractory gastroparesis? Gastroenterol 2000; 118:433-436.
14. Tougas G, Huizing a J D. Gastric pacing as a treatment for intractable gastroparesis: Shocking news? Gastroenterol 1998; 114:456.

Additional References Incorporated

Goyal A, Khurana S, Bhragava S, Abell T L. Gastrointestinal electrical stimulation (GES) can be performed safely with endoscopically placed electrodes. Am J Gastroenterol 2001; 96: S56.
Ayinala S R, Goyal A, Khurana I S, Bhragava I S, Familoni B, Abell T. Response to gastric electrical stimulation performed with temporary electrodes corresponds well to permanent implant. Neurogastroenterol Motility 2002; 14: 422.
Ayinala S R, Al-Juburi A, Familoni B, Abell T L. Gastric emptying and symptom response to gastric electrical stimulation performed with temporary electrodes corresponds well to permanent implantation.
Batista O, Ayinala S, Schmieg R, Abell T L. Temporary gastric electrical stimulation with endoscopically placed electrodes—A report of 27 consecutive patients. Am J Gastroenterol 2003; 98: S226.
Batista O, Ayinala S, Schmieg R, Abell T L. Temporary gastric electrical stimulation improves symptoms of nausea and vomiting in patients with both delayed and non-delayed gastric emptying. Am J Gastroenterol 2003; 98: S50.
Schmieg R, Borman K, Araghizadeh F, Abidi N, Batista O, Abell T L. In patients with disordered post-surgical gastric emptying, temporary gastric electrical stimulation (tempGES) quickly improves symptoms and gastric emptying. Gastroenterol 2004; 126: A771. Presented at Digestive Disease Week and the Meeting of the Society for Surgery of the Alimentary Tract. New Orleans, La., May 15-20, 2004.
Batista O, Schmieg R, Abell T L. Effects of temporary gastric electrical stimulation with endoscopically placed electrodes: a report of 41 consecutive patients. Gastrointestinal Endoscopy, 2004; In press. Presented at American Society for Gastrointestinal Endoscopy, May 16-19, New Orleans, La. Neurogastroenterol Motility, 2004; In press.
Batista O, Schmieg R, Abell T L. Temporary gastric electrical stimulation gastric emptying. Gastroenterol, 2004; 126: A484.

The invention claimed is:

1. A method for treating disorders relating to abnormal gastrointestinal electrical activity in a patient, said method comprising:
   determining frequency and amplitude of natural gastrointestinal electrical activity in the patient;
   calculating a frequency to amplitude ratio from the determined frequency and amplitude; and
   administering electrical stimulation to the gastrointestinal tract of the patient based on the calculated frequency to amplitude ratio, using an endoscopically insertable neural modulation device, to thereby normalize the gastric electrical activity in the patient.

2. The method of claim 1, wherein the administering electrical stimulation comprises applying electrical current having a frequency in the range of 10-100 Hz.

3. The method of claim 1, wherein the administering electrical stimulation comprises applying electrical current in the range of 5 to 20 mAmps and 5 to 10 volts.

4. The method of claim 1, wherein the administering electrical stimulation comprises applying electrical current having a frequency of burst in a range of 5 to 50 burst per minute.

5. The method of claim 1, wherein the administering electrical stimulation comprises applying electrical stimulation to a patient having a natural frequency to amplitude ratio generally in the range of 1 to 100 cycles per minute/millivolts.

6. The method for treating disorders of claim 1, further comprising inserting an electrode into the mucosa of the gastrointestinal tract of the patient for use when determining frequency and amplitude of natural gastrointestinal electrical activity in the patient and for administering electrical stimulation to the gastrointestinal tract of the patient.

7. A method for treating gastrointestinal disorders relating to abnormal gastrointestinal electrical activity in a patient, said method comprising:
   determining frequency and amplitude of natural gastric electrical activity in the patient using an electrode inserted into the mucosa of the patient;
   calculating a frequency to amplitude ratio from the determined frequency and amplitude; and
   administering electrical stimulation to the gastrointestinal tract of the patient based on the calculated frequency to amplitude ratio, using an endoscopically insertable neural modulation device operatively associated with the electrode, to thereby treat the gastrointestinal disorders.

8. The method of claim 7, wherein the gastrointestinal disorders are selected from the group consisting of gastrointestinal disorders, including gastroparesis, dyspepsia, gastro-esophageal reflux and nausea/vomiting of any etiology, along with disorders such as hyperemesis gravidarum of pregnancy, acute and chronic pancreatitis and other pancreato-biliary disorders, including biliary dyskinesia; nausea/vomiting of chemotherapy and/or related to other cancer therapies; rapid and other disordered gastric emptying; metabolic disorders including diabetes; bacterial overgrowth and small bowel dysmotility; constipation, diarrhea and pelvic floor disorders; autonomic disorders; post-transplantation disorders; other post-surgical disorders; and nutritional disorders related to inability to maintain adequate weight. Also included are classic eating disorders, such as anorexia nervosa or bulimia nervosa.

* * * * *